US010585067B2

(12) United States Patent
Horn et al.

(10) Patent No.: US 10,585,067 B2
(45) Date of Patent: Mar. 10, 2020

(54) METHOD FOR NON-DESTRUCTIVE ANALYSIS OF MULTIPLE STRUCTURAL PARAMETERS

(71) Applicant: Atomic Energy Of Canada Limited, Chalk River (CA)

(72) Inventors: Dag Horn, Deep River (CA); Brian A. Lepine, Petawawa (CA); Jia Lei, Deep River (CA)

(73) Assignee: Atomic Energy Of Canada Limited, Chalk River, ON (CA)

( * ) Notice: Subject to any disclaimer, the term of this patent is extended or adjusted under 35 U.S.C. 154(b) by 288 days.

(21) Appl. No.: 15/420,864

(22) Filed: Jan. 31, 2017

(65) Prior Publication Data

US 2017/0219528 A1    Aug. 3, 2017

Related U.S. Application Data

(60) Provisional application No. 62/289,515, filed on Feb. 1, 2016.

(51) Int. Cl.
   *G01N 27/90* (2006.01)
(52) U.S. Cl.
   CPC ..... *G01N 27/9066* (2013.01); *G01N 27/9046* (2013.01); *G01N 27/9073* (2013.01)
(58) Field of Classification Search
   CPC .................................................. G01N 27/9066
   See application file for complete search history.

(56) References Cited

U.S. PATENT DOCUMENTS 5,537,334 A * 7/1996 Attaoui ............. G01N 27/9046
                                                          324/220
5,898,304 A    4/1999 Mandl
                (Continued)

FOREIGN PATENT DOCUMENTS

EP        1521078 A1    6/2005
WO    2016007307 A1    1/2016

OTHER PUBLICATIONS

Extended European Search Report dated Jun. 20, 2017 in respect of European Patent Application No. 17154202.0.
(Continued)

*Primary Examiner* — Manuel A Rivera Vargas
(74) *Attorney, Agent, or Firm* — Kevin Shipley; Fogler, Rubinoff LLP

(57) ABSTRACT

A system and method for non-destructive analysis of a structure. A probe acquires a transient time based reference signal and at least one test signal. The reference signal and test signals are transformed to the frequency domain. The frequency domain test signal can be normalized using the frequency domain reference signal. Parameters of interest are evaluated at each test location by iteratively determining estimated parameter values, generating an estimated frequency domain test signal using the estimated parameter values and determining the convergence between the estimated frequency domain test signal and the normalized frequency domain test signal. The parameters values are determined as the estimated parameter values resulting in a maximized convergence between the estimated signal and the normalized test signal. The parameter values can be used to visualize and model various features of the structure.

20 Claims, 13 Drawing Sheets

(56) References Cited

U.S. PATENT DOCUMENTS

| | | | | |
|---|---|---|---|---|
| 6,037,768 A | * | 3/2000 | Moulder | G01N 27/9046 |
| | | | | 324/202 |
| 2004/0174157 A1 | * | 9/2004 | Goldfine | G01N 27/904 |
| | | | | 324/202 |

OTHER PUBLICATIONS

Pavo, Numerical Calculation Method for Pulsed Eddy-Current Testing, IEEE Transactions on Magnetics, Mar. 2002, pp. 1169-1172, vol. 38, No. 2.

Pan et al., PEC Frequency Band Selection for Locating Defects in Two-Layer Aircraft Structures With Air Gap Variations, IEEE Transactions on Instrumentation and Measurement, Oct. 2013, pp. 2849-2856, vol. 62, No. 10.

Park et al., Differential Pulsed Eddy Current Probe to Detect the Sub Surface Cracks in a Stainless Steel Pipe, 18th World Conference on Nondestructive Testing, Apr. 16-20, 2012, Durban, South Africa.

Safizadeh et al., Time-Frequency Analysis of Pulsed Eddy Current Signals, Journal of Nondestructive Evaluation, Jun. 2001, pp. 73-86, vol. 20, No. 2.

Gombarska et al., Wavelet Based Signal Analysis of Pulsed Eddy Current Signals, University of Zilina, 2011.

Horn et al., Multifrequency Analysis of Eddy Current Data, 18th World Conference on Nondestructive Testing Manuscript Submission, 2004.

Buckley, An Introduction to Eddy Current Testing Theory and Technology, C:\my documents\joe work\tekintro.doc. <https://www.nde-ed.org/EducationResources/CommunityCollege/ Ed . . . >, accessed Jul. 13, 2015.

* cited by examiner

METHOD FOR NON-DESTRUCTIVE ANALYSIS OF MULTIPLE STRUCTURAL PARAMETERS

PRIOR APPLICATION

This application claims the benefit of U.S. Provisional Patent Application No. 62/289,515 filed on Feb. 1, 2016, which is incorporated by reference herein in its entirety.

FIELD

The present subject matter of the teachings described herein relates generally to non-destructive evaluation of structural parameters, and in particular pulsed eddy current testing.

BACKGROUND

Eddy current testing (ET) is a technique that can be used for nondestructive evaluation (NDE) of conductive components. A coil producing a varying magnetic field can be positioned near the conductive component to induce eddy current in the material. Signal analysis processes for analyzing eddy current response signals to obtain component information have been developed over decades of industrial practice (see, for example, V. S. Cecco, G. Van Drunen, and F. L. Sharp, "Eddy Current Manual", Volume 1, AECL Report, AECL-7523 Rev 1, (1983), also Cecco, V. S., and Van Drunen, G., "Recognizing the Scope of Eddy Current Testing", Research Techniques in Nondestructive Testing, Vol. 8, ed., R. S. Sharpe, Academic Press Inc., pp. 269-301 (1985)).

ET was traditionally performed using magnetic fields induced by sinusoidally varying currents. Over time, testing with "pulsed", also known as "transient" eddy currents (PEC or TEC), has become more prevalent for certain applications. However, traditional ET analysis techniques typically cannot be directly applied to pulsed eddy current signals. As a result, quantitative processes for evaluating various structural parameters such as the probe-to-material distance, material thickness, surface extent of flaws, flaw depth, and other geometric measurements using PEC are needed.

Current PEC analysis techniques typically involve correlating specific features of the PEC signal response, such as the time and rate-of-change of the transition from positive to negative voltage, or maximum signal amplitude, to reference samples having known values of the property to be measured. In this approach, unknown samples are assessed using the specific feature of the response signal, effectively constituting a single-variable calibration. In cases where only one quantity is unknown, the existing process is adequate. However, inspected components often have multiple quantities that vary simultaneously, such as the distance between the probe and conductor surface at a flaw of unknown depth and area. Such cases are not quantified by existing PEC analysis techniques.

SUMMARY

This summary is intended to introduce the reader to the more detailed description that follows and not to limit or define any claimed or as yet unclaimed invention. One or more inventions may reside in any combination or subcombination of the elements or process steps disclosed in any part of this document including its claims and figures.

In accordance with one broad aspect of the teachings disclosed herein, there is provided a method for non-destructive analysis of a structure. The method includes acquiring a transient time based continuous reference signal from a reference location on one of the structure and a calibration structure, transforming the transient time based continuous reference signal to a frequency domain reference signal, acquiring a transient time based continuous test signal from a test location on the structure, transforming the transient time based continuous test signal to a frequency domain test signal, identifying at least one parameter of interest of the structure at the test location, and evaluating a parameter value for each of the at least one parameter of interest by: determining an estimated parameter value for each of the at least one parameters, generating a frequency domain estimated signal for the test location using the estimated parameter values, determining a convergence between the estimated signal and the normalized test signal, iteratively adjusting the estimated parameter values and generating an updated frequency domain estimated signal, and for each of the at least one parameters, determining the parameter value as the estimated parameter value for that parameter used to generate the estimated signal that results in a maximized convergence between the estimated signal and the normalized test signal.

In some examples, the method may also include, prior to evaluating the parameter value for each of the at least one parameter of interest, normalizing the frequency domain test signal by, for each frequency of the frequency domain test signal, performing a complex division of a test signal component of the frequency domain test signal at that frequency by a reference signal component of the frequency domain reference signal at that frequency.

In some examples, the method may also include acquiring a transient time based continuous lift-off signal from a location of known lift-off from the one of the structure and the calibration structure, transforming the transient time based continuous lift-off signal to a frequency domain lift-off signal, determining a plurality of lift-off phase angles from the frequency domain lift-off signal, one lift-off phase angle for each frequency of the frequency domain lift-off signal, and prior to determining the convergence between the estimated signal and the test signal, for each frequency of the test signal, rotating a signal component of the estimated signal at that frequency by the lift-off phase angle determined for that frequency.

In some examples, the lift-off phase angle for a particular frequency can be determined by performing a complex division of a lift-off signal component of the frequency domain lift-off signal at the particular frequency by the reference signal component of the frequency domain reference signal for the particular frequency, and determining the lift-off phase angle for the particular frequency from the real and complex signal components resulting from the complex division.

In some examples, the at least one parameter of interest can include a lift-off distance and the method may further include acquiring a plurality of transient time based continuous lift-off calibration signals from a corresponding plurality of lift-off calibration locations, each lift-off calibration location having a different lift-off value from the one of the structure and the calibration structure, transforming each of the transient time based continuous lift-off calibration signals to a frequency domain lift-off calibration signal, generating an estimated lift-off model using the lift-off values for each of the lift-off calibration locations and corresponding frequency domain lift-off calibration signal, and generating the frequency domain estimated signal for the test location by applying the estimated lift-off model to the estimated parameter value for the lift-off distance.

In some examples, the at least one parameter of interest can include at least two parameters, and the parameter values for each of the at least two parameters can be evaluated simultaneously.

In some examples, the at least one parameter can include at least one of a structure thickness, a feature surface extent, a feature shape, a feature depth, a deposit thickness, a lift-off variation, a permeability variation, a conductivity variation, a conductor-to-conductor gap.

In some examples, the frequency domain estimated signal can be generated by determining a skin depth of the structure at each frequency of the test signal, and generating the frequency domain estimated signal by modelling a test signal estimate at the test point using the calculated skin depth for each frequency of the test signal and the estimated parameter values.

In some examples, variations in the skin depth can be determined by: measuring a first response signal amplitude at the test location in response to a first interrogation signal from a first lift-off distance; measuring a second response signal amplitude at the test location in response to a second interrogation signal from a second lift-off distance where the first lift-off distance and second lift-off distance can have a defined lift-off pair difference; and determining the skin depth variation from the first response signal amplitude, the second response signal amplitude and the lift-off pair difference.

In some examples, the convergence between the estimated signal and the test signal can be determined by for each frequency of the test signal, determining a residual signal value based on the difference between the estimated signal and the test signal, and determining the convergence between the estimated signal and the normalized test signal using a sum of the residual signal values for each frequency.

In some examples, the method may also include generating a frequency domain final estimated signal using the determined parameter values for the at least one parameter, and concurrently displaying the frequency domain final estimated signal and the frequency domain test signal.

In some examples, the method may also include acquiring at least one additional transient time based continuous test signal, each additional transient time based continuous test signal being acquired from an additional test location on the structure, transforming each of the additional transient time based continuous test signals to a frequency domain additional test signal, and for each frequency domain additional test signal, evaluating an additional parameter value of the at least one parameter of the structure at the corresponding additional test location by determining an additional estimated parameter value for each of the at least one parameters, generating an additional frequency domain estimated signal for that additional test location using the additional estimated parameter values, determining an additional convergence between the additional estimated signal and the additional test signal, iteratively adjusting the additional estimated parameter values and generating an updated additional frequency domain estimated signal, and for each of the at least one parameters, determining the additional parameter value as the additional estimated parameter value for that parameter used to generate the additional estimated signal that results in a maximized convergence between the additional estimated signal and the additional test signal.

In some examples, the method may further include modelling the structure using the parameter values determined for each test location of the structure, and displaying the modelled structure.

In some examples, acquiring the transient time based continuous reference signal may include acquiring a reference response signal from a first pulsed eddy current signal applied at the reference location, and acquiring the transient time based continuous test signal may include acquiring a test response signal from a second pulsed eddy current signal applied at the test location on the structure.

In some examples, acquiring the transient time based continuous lift-off signal may include acquiring a lift-off response signal from a third pulsed eddy current signal applied at the location of known lift-off from the structure.

In accordance with another broad aspect of the teachings described herein, which may be used alone or in combination with any other aspects, there is provided a system for non-destructive analysis of a structure. The system can include a function generator for generating an interrogation waveform, an interrogation unit coupled to the function generator, the interrogation unit including a signal transmitter and a sensor, wherein the signal transmitter can be configured to apply the interrogation waveform to a reference location on one of the structure and a calibration structure, and apply the interrogation waveform to a test location on the structure, and the sensor can be configured to acquire a transient time based continuous reference signal from the reference location, and acquire a transient time based continuous test signal from the test location, a processor coupled to the probe, the processor configured to transform the transient time based continuous reference signal received from the sensor to a frequency domain reference signal, transform the transient time based continuous test signal received from the sensor to a frequency domain test signal, identify at least one parameter of interest of the structure at the test location, and evaluate a parameter value for each of the at least one parameters of interest by determining an estimated parameter value for each of the at least one parameters, generating a frequency domain estimated signal for the test location using the estimated parameter values, determining a convergence between the estimated signal and the test signal, iteratively adjusting the estimated parameter values and generating an updated frequency domain estimated signal, and for each of the at least one parameters, determining the parameter value as the estimated parameter value for that parameter used to generate the estimated signal that results in a maximized convergence between the estimated signal and the normalized test signal, and a display coupled to the processor for displaying the determined parameter values of the structure.

In some examples, the processor can be further configured to, prior to evaluating the parameter value for each of the at least one parameters of interest, normalize the frequency domain test signal by, for each frequency in the frequency domain test signal, performing a complex division of a test signal component of the frequency domain test signal at that frequency by a reference signal component of the frequency domain reference signal at that frequency.

In some examples, the transmitter can be further configured to apply the interrogation waveform at a location of known lift-off from the one of the structure and the calibration structure, the sensor can be further configured to acquire a transient time based continuous lift-off signal from the location of known lift-off, and the processor can be further configured to transform the transient time based continuous lift-off signal received from the sensor to a frequency domain lift-off signal, determine a plurality of lift-off phase angles from the frequency domain lift-off signal, one lift-off phase angle for each frequency of the frequency domain lift-off signal, and prior to determining the convergence between the estimated signal and the test signal, for each frequency of the test signal, rotate a signal component of the estimated signal at that frequency by the lift-off phase angle determined for that frequency.

In some examples, the processor can be configured to determine the lift-off phase angle for a particular frequency by performing a complex division of a lift-off signal component of the frequency domain lift-off signal at the particular frequency by the reference signal component of the frequency domain reference signal for the particular frequency, and determining the lift-off phase angle for the particular frequency from the real and complex signal components resulting from the complex division.

In some examples, the at least one parameter of interest may include a lift-off distance, the transmitter can be further configured to apply the interrogation waveform at a plurality of lift-off calibration locations, each lift-off calibration location having a different lift-off value from the one of the structure and the calibration structure, the sensor can be further configured to acquire a corresponding plurality of transient time based continuous lift-off calibration signals from the plurality of lift-off calibration locations, and the processor can be further configured to transform each of the transient time based continuous lift-off calibration signals to a frequency domain lift-off calibration signal, generate an estimated lift-off model using the lift-off values for each of the lift-off calibration locations and corresponding frequency domain lift-off calibration signal, and generate the frequency domain estimated signal for the test location by applying the estimated lift-off model to the estimated parameter value for the lift-off distance.

In some examples, the at least one parameter of interest can include at least two parameters and the processor can be configured to evaluate the parameter values for each of the at least two parameters simultaneously.

In some examples, the at least one parameter can include at least one of a structure thickness, a feature surface extent, a feature shape, a feature depth, a deposit thickness, a lift-off variation, a permeability variation, a conductivity variation, a conductor gap.

In some examples, the processor can be configured to generate the frequency domain estimated signal by determining a skin depth of the structure at each frequency of the test signal, and generating the frequency domain estimated signal by modelling a test signal estimate at the test point using the calculated skin depth for each frequency of the test signal and the estimated parameter values.

In some examples, the processor can be configured to determine variations in the skin depth by: measuring a first response signal amplitude at the test location in response to a first interrogation signal from a first lift-off distance; measuring a second response signal amplitude at the test location in response to a second interrogation signal from a second lift-off distance where the first lift-off distance and second lift-off distance can have a defined lift-off pair difference; and determining the skin depth variation from the first response signal amplitude, the second response signal amplitude and the lift-off pair difference.

In some examples, the processor can be configured to determine the convergence between the estimated signal and the test signal by for each frequency of the test signal, determining a residual signal value based on a difference between the estimated signal and the test signal, and determining the convergence between the estimated signal and the test signal using a sum of the residual signal values for each frequency.

In some examples, the processor can be further configured to generate a frequency domain final estimated signal using the determined parameter values for each of the at least one parameters, and concurrently display the frequency domain final estimated signal and the frequency domain test signal using the display.

In some examples, the transmitter can be further configured to apply the interrogation waveform to at least one additional test location on the structure, the sensor can be further configured to acquire at least one additional transient time based continuous test signal, each additional transient time based continuous test signal being acquired from a corresponding additional test location, the processor can be further configured to transform each of the additional transient time based continuous test signals received from the sensor to a corresponding frequency domain additional test signal, for each frequency domain additional test signal, and for each frequency domain additional test signal, evaluate an additional parameter value of the at least one parameter of the structure at the corresponding additional test location by determining an additional estimated parameter value for each of the at least one parameters, generating an additional frequency domain estimated signal for that additional test location using the additional estimated parameter values, determining an additional convergence between the additional estimated signal and the additional test signal, iteratively adjusting the additional estimated parameter values and generating an updated additional frequency domain estimated signal, and for each of the at least one parameters, determining the additional parameter value as the additional estimated parameter value for that parameter used to generate the additional estimated signal that results in a maximized convergence between the additional estimated signal and the normalized additional test signal.

In some examples, the processor can be further configured to model the structure using the parameter values determined for each test location of the structure and display the modelled structure using the display.

In some examples, the function generator can be configured to generate the interrogation waveform to include at least one pulsed wave signal.

Other aspects and features of the teachings disclosed herein will become apparent, to those ordinarily skilled in the art, upon review of the following description of the specific examples of the present disclosure.

DRAWINGS

The drawings included herewith are for illustrating various examples of articles, methods, and apparatuses of the teaching of the present specification and are not intended to limit the scope of what is taught in any way.

DETAILED DESCRIPTION

Figure 1:
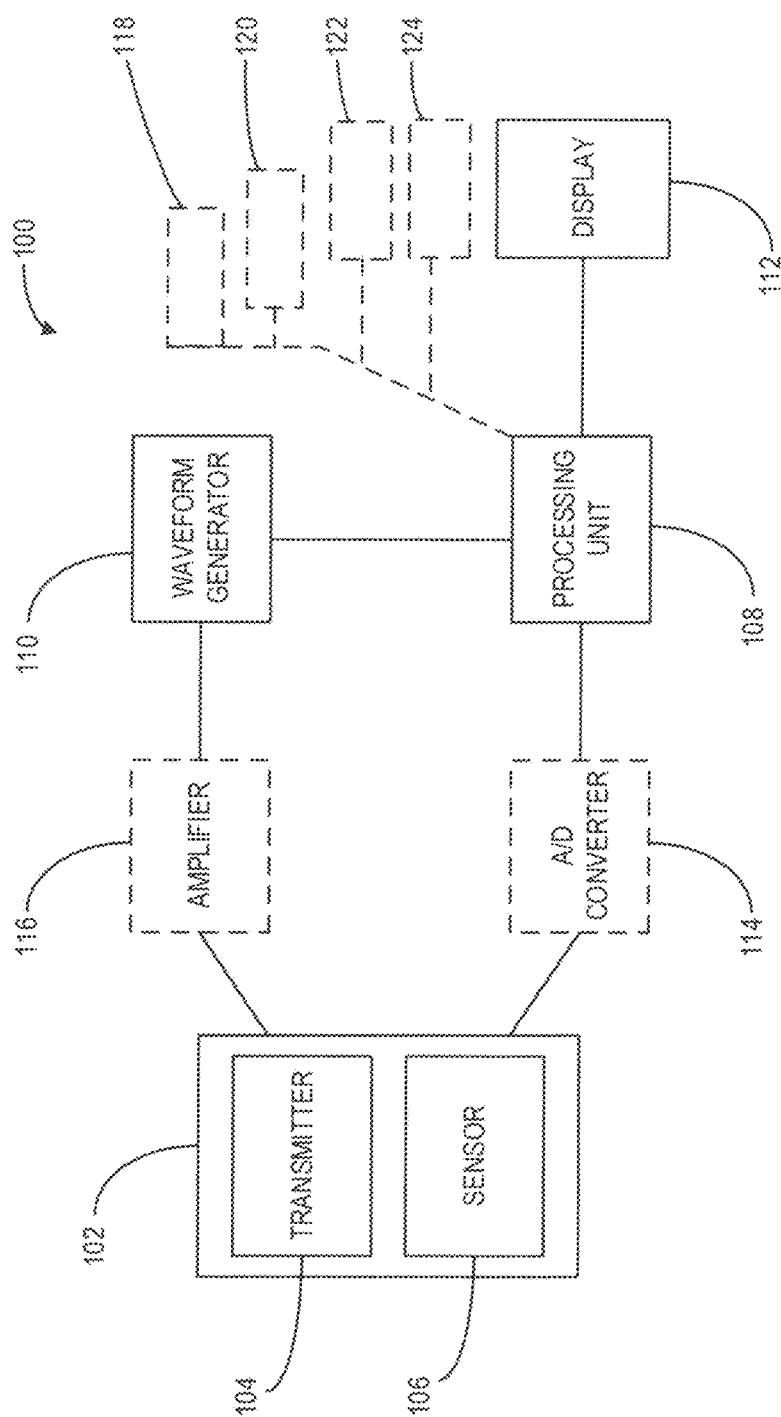
FIG. 1 is a block diagram of one example of a system for non-destructive analysis of a structure.

Various apparatuses or processes will be described below to provide an example of an embodiment of each claimed invention. No embodiment described below limits any claimed invention, and any claimed invention may cover processes or apparatuses that differ from those described below. The claimed inventions are not limited to apparatuses or processes having all of the features of any one apparatus or process described below, or to features common to multiple or all of the apparatuses described below. It is possible that an apparatus or process described below is not an embodiment of any claimed invention. Any invention disclosed in an apparatus or process described below that is not claimed in this document may be the subject matter of another protective instrument, for example, a continuing patent application, and the applicants, inventors or owners do not intend to abandon, disclaim or dedicate to the public any such invention by its disclosure in this document.

Eddy current testing and pulsed eddy current testing are nondestructive testing techniques that use electromagnetic inductance to detect and evaluate structural parameters in conductive materials. Examples of structural parameters can include remaining conductor thickness, lift-off, deposit thickness, permeability changes, and various parameters of surface and sub-surface features, like extent and depth, among many others. As used herein the term feature can also include flaws which may limit the useful life of a specimen or component.

Pulsed eddy current testing may provide certain advantages over classical eddy current testing. For instance, applying a pulsed or transient interrogation signal to the structure may allow response signals to be collected with signal components for a wide range of frequencies. The use of low frequencies may increase the skin depth for penetration of currents into the material, which can be of advantage in high-conductivity or high-permeability materials. The use of very high frequencies may be more sensitive to lift-off and near-surface features. Detection and characterization of defects at large lift-off and through multi-layer specimens may also become possible. However, some present-day techniques for pulsed eddy current testing may be suboptimal for quantitative analysis of multiple parameters and determining dimensional results of multiple structural parameters. These methods may tend to focus on a specific feature of the pulsed eddy current signal response, and correlate changes in that feature to a specific parameter. Some advanced techniques such as Principal Component Analysis have been attempted to relate parameter changes to slight variations in the signal, but these results can be confused by multiple parameters.

The embodiments described herein provide systems and methods for non-destructive analysis of a structure. At least some of the embodiments may be applied to analyze and evaluate multiple parameters of a structure. At least some of the described embodiments may permit simultaneous extraction/evaluation of several structural parameters (such as feature depth and feature extent) which, to the inventors' knowledge, has not been possible with existing pulsed eddy current analysis techniques. Furthermore, at least some of the disclosed embodiments may make use of signal information from substantially the entire signal response, and optionally the entire signal response, rather than focusing on specific signal features or selected frequencies. The use of greater signal information may help increase the reliability and accuracy of parameter evaluation.

Also disclosed herein are some examples of systems and methods for transforming pulsed eddy current signal responses into geometrical measurement quantities. These geometrical measurement quantities can be used to model the structure being tested. A modelled structure can be displayed to a user in any suitable manner, including, for example, by providing a visual representation of the structure being analyzed. This may help the user to visually analyze subsurface parameters of the structure non-destructively.

Optionally, the disclosed embodiments may be used to inspect high-conductivity (e.g. aluminum) or high-permeability (e.g. carbon steel) materials for various parameters. These parameters may be used to characterize the structure under analysis or defects therein (e.g. thickness parameters and parameters related to structural defects). The disclosed embodiments may help facilitate inspection techniques in various fields, such as inspection of insulated oil/gas pipelines, corroded NRU reactor reflector walls, and inspection of various vehicles such as aircraft and naval vessel hulls.

Optionally, the embodiments described herein may use a minimization technique to compare acquired response signals to calculated/modelled response signals. The minimization technique may compare signal components of the acquired signals at various frequencies to calculated signal components at the corresponding frequencies. In some cases, the minimization technique may consider all available frequencies of the acquired response signals. Alternatively, in some instances the minimization technique may consider only some of the available frequencies of the acquired response signals. The embodiments may be used to simultaneously, or at least substantially simultaneously, evaluate a plurality of structural parameters (e.g. thickness, flaw depth, flaw extent etc.) taking into account the entire transient signal response rather than just a specific signal feature.

In some cases, the embodiments disclosed herein may also be applied under conditions of varying lift-off, e.g. due to insulating coverings or corrosion layers, while at least partially accounting for the variations in lift-off.

Optionally, when analyzing a structure, a reference location of the structure can be identified. The reference location may also be referred to, but not limited to, as a "balance point" or "no defect" location. A signal transmitter (e.g. a signal probe) can apply an interrogation waveform at the reference location. The interrogation waveform may be generated using any suitable function or waveform generator. Various types of interrogation waveforms may be used, such as a pulsed signal (e.g. a periodic square waveform or step function) suitable for pulsed eddy current analysis. In some cases, a calibration structure may be used as the reference location. The calibration structure may be a structure specifically manufactured to have properties similar to the original properties or expected properties of materials known to be present in the structure to be tested. The calibration structure may contain one or more parameters of interest with known structural properties (e.g. shape, depth, extent etc.) characteristic of past or postulated features that have occurred or could occur in the test structure, that may be use to adjust input parameters for specific features based on their acquired response signals.

Optionally, a corresponding time-based reference response signal can be acquired from the reference location using a signal sensor. In some cases, the signal transmitter and signal sensor can be implemented using a single probe, for instance using a side-by-side or a concentric pair of transmit and receive coils. Optionally a single coil may be used as both a transmitter and signal sensor. The time-based reference response signal can then be transformed to a frequency domain reference signal using any suitable method. The time-based signal may be acquired as a continuous signal and transformed to a discrete frequency domain signal by any suitable A/D converter and/or a processing unit.

Optionally, the interrogation waveform can also be applied at a test location on the structure. As used herein, a test location generally refers to any location of the structure having one or more unknown or uncertain parameters a user is interested in evaluating. The corresponding time-based test response signal can be acquired, and it too can optionally be transformed to a frequency domain test signal. The frequency domain test signal can be analyzed to evaluate the parameters of the structure at the test location.

Optionally, the frequency domain test signal can be normalized using the frequency domain reference signal. The frequency domain test signal can be normalized by, for each frequency of the frequency domain test signal, performing a complex division of a test signal component for that frequency (in the frequency domain test signal) by a reference signal component for the same frequency (in the frequency domain reference signal). The normalized frequency domain test signal with a plurality of normalized test signal components (having both real and imaginary component values) can then be used to evaluate at least some of the parameters of the structure at the test location.

Optionally, one or more parameters of interest can be identified for evaluation. The parameters of interest may include any suitable parameters of interest to a user, including, for example, one or more of a structure thickness, a feature surface extent, a feature shape, a feature depth, a deposit thickness, a lift-off variation, a permeability variation, a conductivity variation, and a conductor gap among others. The parameters of interest may be selected based on a variety of factors, including, for example, the type of evaluation being undertaken, or from parameters that are currently unknown or uncertain. In some cases, a parameter of interest may be identified on the basis of previous parameter evaluations at the same or other test locations on the same structure.

In general, at least some aspects of the embodiments described herein can be applied to evaluate the identified parameters of interest simultaneously. For example, rather than evaluating individual structural parameters on the basis of signal features thought to correspond to those individual parameters, a plurality of parameters can be simultaneously analyzed using the plurality of normalized test signal components for each interrogation. That is, the plurality of parameters of interest may be simultaneously evaluated (or at least substantially simultaneously, allowing for processing time, serial processing of the signals in the processing unit, etc.) to provide a fuller picture of the structure being analyzed. This may also account for variations in response signals that may be dependent on multiple structural parameters.

The parameters may be evaluated using a variety of suitable techniques. In accordance with one aspect of the teachings described herein, to evaluate the parameters, an initial estimated parameter value may be determined for each parameter of interest. Using the estimated parameter values, an estimated frequency domain signal can be generated for the test location. The estimated frequency domain signal can be generated to reflect a response signal expected to be obtained for that test location, using the particular interrogation waveform, if the estimated parameter values were correct. The estimated frequency domain signal can then be compared to the (actual) normalized test signal.

Optionally, a difference or error or convergence between the estimated signal and the normalized test signal can be determined using any suitable method. For instance, a plurality of signal component residuals between the signals components of the normalized test signal and the corresponding estimated signal components can be determined. Using the plurality of signal components residuals, the difference or error or convergence can be determined. For example, the difference or error may be determined as the sum of the squares of the plurality of signal component residuals. Various techniques may be applied to determine the difference or convergence (distance or closeness or error, or similarity etc.) between the estimated signal and the normalized test signal, but for clarity the following description will generally refer to determining a convergence between the estimated signal and the normalized test signal.

If the difference or error between the estimated signal and the normalized test signal is greater than a desired convergence (i.e. the convergence is less than the desired convergence), the estimated parameter values can be adjusted. An updated frequency domain estimated signal can then be generated using the adjusted estimated parameter values. This process of adjusting estimated parameter values, generating an updated frequency domain estimated signal, and comparing the normalized test signal to the estimated signal can be repeated iteratively. Where multiple parameters of interest are being evaluated, one or more of the estimated parameter values may be adjusted each iteration.

When the desired convergence between the estimated signal and the normalized test signal is obtained, the parameter values for at least some of, and optionally for each of the parameters of interest, can be determined. Optionally, the parameter values can be determined as the estimated parameter values for each parameter of interest used to generate the estimated signal that resulted in the desired convergence (i.e. a minimized difference between the estimated signal and the normalized test signal). In some cases, the desired/maximized convergence (or minimized difference) may be an absolute minimum difference between the test signal and the estimated signal (i.e. the evaluation may continue until each possible combination of estimated parameter values is evaluated and the absolute minimum difference is found). In other cases, the maximized convergence or minimized difference may be identified when a desired convergence criterion is satisfied, and the evaluation may stop once the desired convergence is obtained.

Optionally, the determined parameter values may be stored in a database for further investigation. In some cases, the determined parameters may be displayed to a user. In some cases, the determined parameters may also be used to generate a model of the structure. For example, the analysis process can be repeated for a plurality of additional test locations. The determined parameter values for each test location can be associated with the corresponding test location. Once a desired portion of the structure has been analyzed, for instance a 2D scan of the structure surface, a model can be generated to represent one or more of the determined structural parameters. A user may then analyze the structural parameters, for example to identify the existence or extent of defects, or to identify unexpected or undesired parameter values that may indicate potential future development of defects.

Optionally, in some embodiments, a lift-off calibration may be used to help account for variations in lift-off or unknown lift-off at the test locations. The interrogation waveform can be applied to a location of known lift-off from the surface of the structure (or from the surface of a calibration structure). For example, a location of known lift-off may be created by a user placing a non-conductive material of known thickness between the interrogation unit and the surface of the structure or calibration structure. A time-based lift-off signal can then be acquired from the location of known lift-off and transformed to a discrete frequency domain lift-off signal.

A plurality of lift-off phase angles can be determined from the frequency domain lift-off signal. For each frequency of the frequency domain lift-off signal, a corresponding lift-off phase angle can be determined. The lift-off phase angle for a particular frequency may be determined by performing a complex division of the lift-off signal component at that frequency by the reference signal component for that frequency. The lift-off phase angle can then be determined using the real and complex residual values from the complex division. The lift-off phase angles for each frequency can be used to rotate the estimated signal components for the corresponding frequency prior to determining the difference between that estimated signal component and the corresponding normalized test signal component.

The use of a pulsed eddy current signal, such as a step function, ensures that in a single signal acquisition, signal components for a plurality of frequencies are acquired. In contrast, with traditional eddy current testing, repeated interrogations and signal acquisition steps must be performed to capture signal components corresponding to a range of frequencies. Accordingly, acquired time-based response signals used in embodiments described herein may provide a larger number of signal components that can be used to evaluate a test response signal. By simultaneously analyzing a large number of signal components, greater accuracy and reliability of the parameter evaluation may be achieved.

The example embodiments of the systems and methods described in accordance with the teachings herein may be implemented as a combination of hardware or software. In some cases, the example embodiments described herein may be implemented, at least in part, by using one or more computer programs, executing on one or more programmable devices comprising at least one processing element, and at least one data storage element (including volatile and non-volatile memory and/or storage elements). These devices may also have at least one input device (e.g. a keyboard, mouse, a touchscreen, and the like), and at least one output device (e.g. a display screen, a printer, a wireless radio, and the like) depending on the nature of the device.

It should also be noted that there may be some elements that are used to implement at least part of one of the embodiments described herein that may be implemented via software that is written in a high-level procedural language such as object oriented programming. Accordingly, the program code may be written in C, C++ or any other suitable programming language and may comprise modules or classes, as is known to those skilled in object oriented programming. Alternatively, or in addition thereto, some of these elements implemented via software may be written in assembly language, machine language or firmware as needed. In either case, the language may be a compiled or interpreted language.

At least some of these software programs may be stored on a storage media (e.g. a computer readable medium such as, but not limited to, ROM, magnetic disk, optical disc) or a device that is readable by a general or special purpose programmable device. The software program code, when read by the programmable device, configures the programmable device to operate in a new, specific and predefined manner in order to perform at least one of the methods described herein.

Furthermore, at least some of the programs associated with the systems and methods of the embodiments described herein may be capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

Referring now to FIG. 1, shown therein is a block diagram of one example of a system 100 for non-destructive analysis of a structure. System 100 includes an interrogation unit 102, a processing unit 108, a function generator 110, in the form of a waveform generator, and a display 112. Optionally, in some embodiments, system 100 can also include an analog to digital converter 114 and an amplifier unit 116, as illustrated using dashed lines in FIG. 1.

Interrogation unit 102 can be any suitable apparatus and may include a probe or signal transmitter 104 and a sensor or signal receiver 106. The signal transmitter 104 can be used to apply an interrogation waveform to the structure at various locations. The signal transmitter 104 may include a coil through which a varying current can flow. The varying current may be in the form of a transient waveform, such as a step function. The varying current may induce a magnetic field as a result of the current running through the coil. When the signal transmitter 104 is placed in proximity to the structure to be examined, the magnetic field may induce eddy currents in the structure.

The sensor 106 can be used to detect the induced eddy current response from the structure. The sensor 106 may also include a corresponding coil. The sensor 106 can be placed near the surface of the structure, adjacent to the signal transmitter 104. The interrogation unit 102 may include a side-by-side transmit-receive pair of coils acting as the signal transmitter 104 and the sensor 106. For example, the interrogation unit 102 may include a side-by-side transmit-receive pair of 20-mm diameter coils, with 20 mm centre-to-centre separation. Various other configurations of the interrogation unit 102 may be used, with different sizes of coils or different distances between the sensor 106 and the transmitter 104. In some cases, a single coil may be used as both a transmitter 104 and sensor 106.

One example of a suitable interrogation unit is a Custom PEC Reflection Probe: Model number P02-2000-003/P02-3000-002, manufactured by Canadian Nuclear Laboratories.

The interrogation unit 102 can be communicably connected to the processing unit 108 so that the processing unit 108 can receive the response signals acquired by sensor 106 from the interrogation unit 102. The response signals may optionally be received by sensor 106 as analog or continuous time-based signals.

Optionally, the acquired continuous time-based signals can be digitized, for example using analog-to-digital converter 114. In some cases, the analog to digital converter 114 can be circuitry incorporated into the processing unit 108. In other cases, the analog to digital converter 114 may be a separate component coupled to the interrogation unit 102 and the processing unit 108. For instance, the acquired response signal received from the sensor 106 may be digitized at 0.25 MHz (i.e. every 4 microseconds) as illustrated in the example shown in FIG. 5B. Various other possible digitization parameters may also be used.

The processing unit 108 can control the operation of various components of system 100 such as the interrogation unit 102, waveform generator 110, the display 112, the A/D converter 114, and the amplifier 116. The processing unit 108 may be any suitable processor, controller or digital signal processor that can provide sufficient processing power depending on the configuration, purposes and requirements of the system 100 as is known by those skilled in the art. For example, the processing unit 108 may be a high performance general processor. In alternative embodiments, the processing unit 108 may include more than one processor with each processor being configured to perform different dedicated tasks. In alternative embodiments, specialized hardware can be used to provide some of the functions provided by the processing unit 108.

The system 100 may also include various additional components coupled to, or integrated with, the processing unit 108 such as a user interface 118, interface unit 120, a wireless unit 122, and a memory unit 124. The memory unit can include software code for implementing an operating system and various programs. Many components of the system 100 can be implemented using a desktop computer, a laptop, a mobile device, a tablet, and the like.

The user interface 118 can include at least one of a mouse, a keyboard, a touch screen, a thumbwheel, a track-pad, a track-ball, a card-reader, voice recognition software and the like again depending on the particular implementation of system 100. In some cases, some of these components can be integrated with one another. A user may interact with the user interface 118 to identify and modify calibration or operating parameters, such as the thickness of a non-conductive material placed between the interrogation unit 102 and the surface of a structure when determining lift-off phase angles. The user may also interact with the user interface 118 to identify parameters of interest, or known parameters of the structure being examined. The user interface 118 may also include at least one of a microphone, a speaker, and a printer, for example.

The interface unit 120 can be any interface that allows the system 100 to communicate with other devices or computers. In some cases, the interface unit 120 can include at least one of a serial port, a parallel port or a USB port that provides USB connectivity, and the like. The interface unit 120 can also include at least one of an Internet, Local Area Network (LAN), Ethernet, Firewire, modem or digital subscriber line connection. Various combinations of these elements can be incorporated within the interface unit 120.

The wireless unit 122 can be a radio that communicates utilizing CDMA, GSM, GPRS or Bluetooth protocol according to standards such as IEEE 802.11a, 802.11b, 802.11g, or 802.11n, and the like. The wireless unit 122 can be used by the processing unit 108 to communicate with other devices or computers.

The memory unit 124 can include RAM, ROM, one or more hard drives, one or more flash drives or some other suitable data storage elements such as disk drives, etc. The memory unit 124 may be used to store an operating system and programs as is commonly known by those skilled in the art. For instance, the operating system provides various basic operational processes for the processing unit 108. The programs include various user programs so that a user can interact with the processing unit 108 to perform various functions such as, but not limited to, acquiring response signals using the interrogation unit 102, viewing and manipulating determined parameter values for the structure, adjusting operating parameters related to data analysis (e.g. convergence condition, parameters of interest) as well as sending messages as the case may be.

The display 112 can be any suitable display that provides visual and/or audible information depending on the configuration of the system 100. For instance, the display 112 can be a cathode ray tube, a flat-screen monitor and the like if the processing unit 108 is a desktop computer. In other cases, the display 112 can be a display suitable for a laptop, tablet or handheld device such as an LCD-based display and the like. The display 112 may be used to display determined parameter values for a structure, as well as modelled structures generated in embodiments described herein.

Figure 5A:
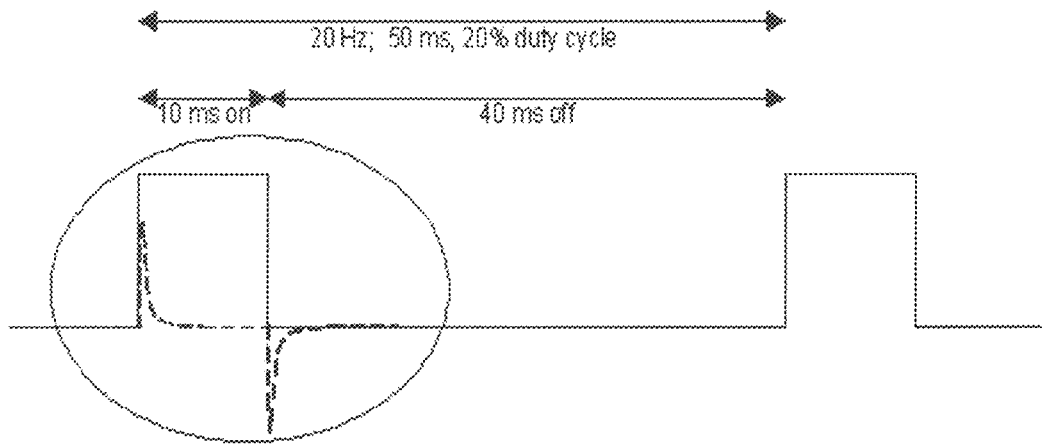
FIG. 5A is a plot of one example of an interrogation signal waveform that can be applied to a structure.

The waveform or function generator 110 can be used to generate an interrogation waveform that can be used to drive the transmitter 104. In general, the function generator 110 can be configured to generate a step function waveform voltage to excite the probe 104. For instance, the function generator 110 may generate a 10V square waveform of 20% duty cycle at a repetition rate of 20 Hz, i.e., 10 ms on and 40 ms off as shown in FIG. 5A below. Various aspects of the interrogation waveform generated by the function generator 110 may be modified depending on the desired operating parameters, such as the voltage level, duty cycle, period etc. For example, depending on the number/range of the frequencies a user wants to evaluate, the pulse width may be modified.

In some cases, the function generator 110 can be implemented in software stored in the memory unit for operation on the processing unit 108. In other cases, an external function generator 110 can be used to generate the interrogation waveform. In such cases, the function generator 110 can be coupled to the interrogation unit 102 to drive the interrogation signal through transmitter 104. The function generator 110 may be controlled either directly, through user input to the function generator 110, or through coupling to the processing unit 108. The amplifier 116 can be used to adjust the signal level of the interrogation waveform generated by the function generator 110, as needed.

Figure 2:
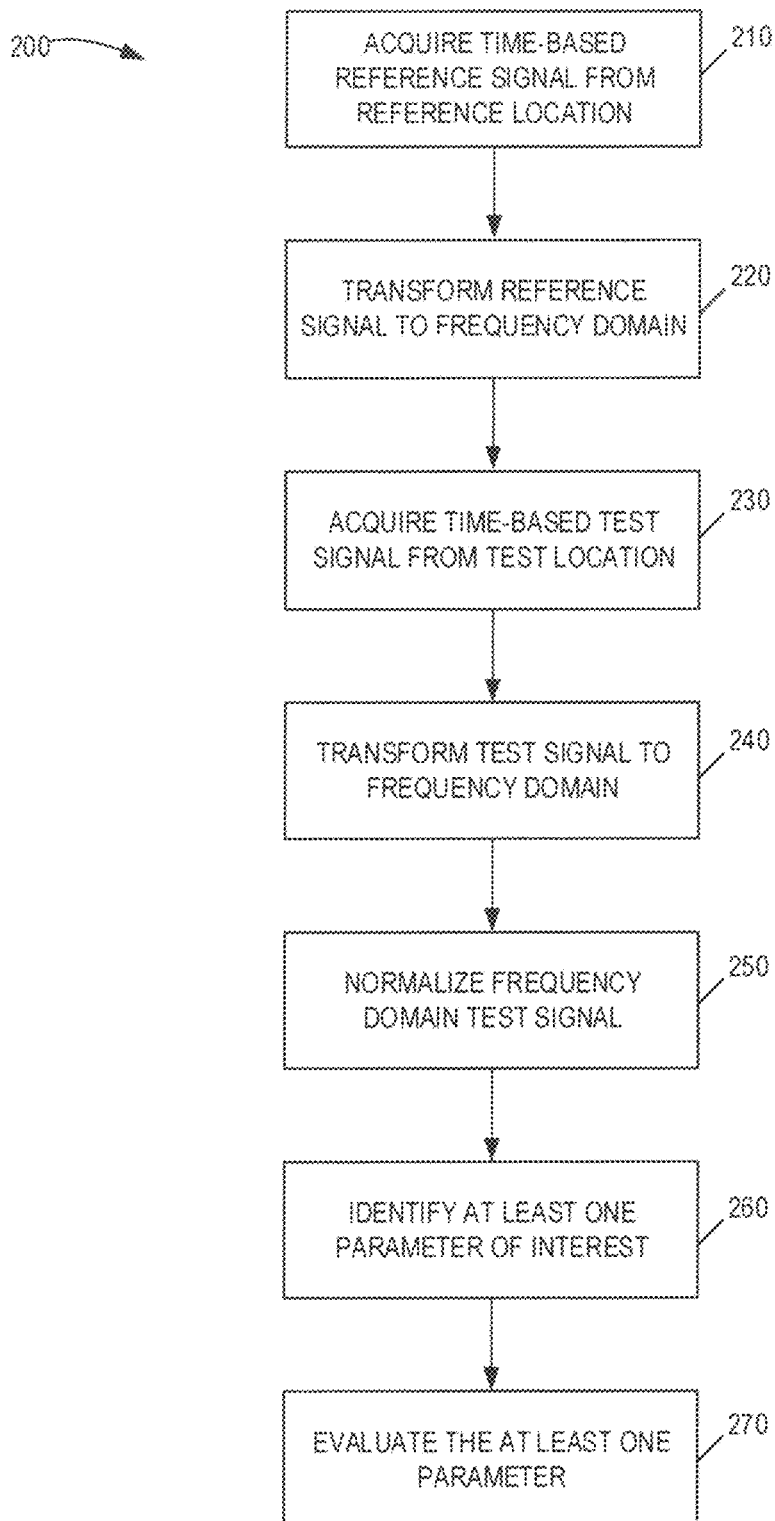
FIG. 2 is a flowchart of one example of a method for non-destructive analysis of a structure.

Referring now to FIG. 2, shown therein is a flowchart of one example of a method 200 for non-destructive analysis of a structure. Method 200 is an example of a method for non-destructive analysis of a structure that may be implemented using system 100.

At 210, a transient time based continuous reference signal can be acquired from a reference location on the structure or a calibration structure. The reference location generally refers to a pre-determined defect-free reference point of the structure being evaluated or of a calibration structure. The calibration structure may be specifically manufactured for analysis of a particular structure, or a particular type of structure (e.g. a structure manufactured of a particular material). For example, the reference location may be chosen to be a location of the structure having full thickness as determined by an independent measurement. The reference location may also be referred to as the "balance point" or balance location and/or the "no-defect" location.

The reference signal can be acquired using the interrogation unit 102. An interrogation waveform, such as a step function or other pulsed eddy current analysis signal waveform can be applied at the reference location using the transmitter 104. An example of an interrogation waveform that may be applied by the transmitter 104 is described with reference to FIG. 5A.

Referring now to FIG. 5A, shown therein is a plot of one example of an interrogation waveform that can be used to generate response signals in a structure. The example interrogation waveform shown by the solid line in FIG. 5A is a 10V square waveform with a 20% duty cycle at a repetition rate of 20 Hz (i.e. an interrogation waveform with a 10 ms active period and a 40 ms inactive period).

The interrogation waveform may be generated using function generator 110 as explained above. The interrogation waveform can be used to drive the transmitter 104. Various different interrogation waveforms, such as waveforms suitable for pulsed eddy current testing can be used. The transmitter 104 can be used to induce an eddy current response in the structure by placing the transmitter 104 at the reference location. A reference response signal can then be acquired from the reference location using the sensor 106. An example of an acquired response signal is described below with reference to FIG. 5B.

Referring again to FIG. 2, at 220 the transient time based continuous reference signal can be converted to a frequency domain reference signal. For instance, the acquired continuous reference signal can be digitized using analog to digital converter 114 or by processing unit 108 to generate a discrete time-based reference signal. The discrete time-based reference signal may then be transformed to the frequency domain using a transform such as a Discrete Fourier Transform or Fast Fourier Transform (FFT), or other transforms that would be apparent to a skilled reader. In some cases, the time-based reference signal may not be digitized prior to being transformed to the frequency domain.

Figure 5B:
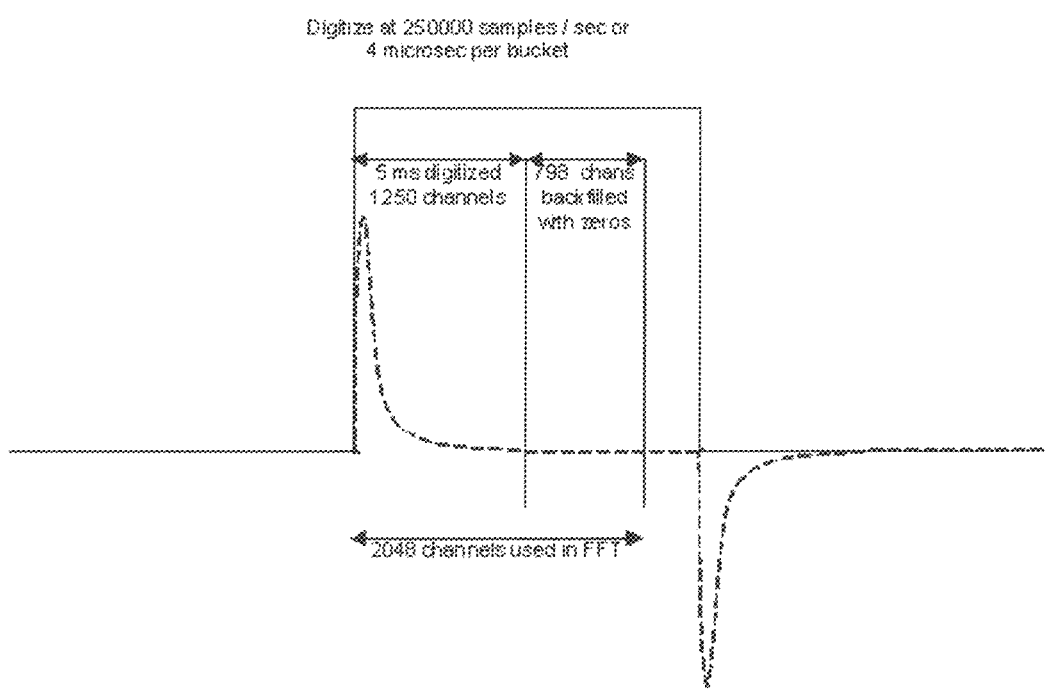
FIG. 5B is a plot of an example of a response signal waveform that may be received from the structure.

Referring now to FIG. 5B, shown therein is a plot of an example of a response signal waveform that may be received from a location in the structure. The response signal waveform shown by the dashed curve in FIG. 5B is a continuous, time-based response signal obtained using a sensor 106 placed at the reference location when the waveform shown in FIG. 5A is used. As FIG. 5B indicates, the continuous time-based response signal may be digitized using various sampling rates, such as 4 micro-seconds (i.e. 0.25 MHz) in the example shown.

A transform can then be used to convert the discrete time-based response signal to the frequency domain. The transform may generate complex frequency domain signal components for a plurality of frequencies. The particular frequencies for which frequency domain signal components are generated may depend on the operating parameters such as the sampling rate and the number of channels used in the transform. For example, as shown in FIG. 5B, a 2048 channel fast Fourier transform with a 0.25 MHz sampling rate may provide a sequence of frequency signal components for frequencies incremented by approximately 122 HZ between adjacent frequencies. As will be apparent to a skilled reader, various other configurations and operating parameters may be used, resulting in different ranges and increments of frequencies. Similarly, alternative transformations may be used to convert the acquired continuous time-based response signal to a frequency domain response signal.

Referring again to FIG. 2, at 230 a transient time based continuous test signal can be acquired from a test location on the structure. The test signal can be acquired in the same manner as with the reference response signal acquired at 210. An interrogation waveform can be applied to the test location using the transmitter 104. The test location may be selected as a location of interest on the structure where one or more parameters of interest are to be evaluated. In some cases, a plurality of test locations may be identified and test signals may be acquired from each test location.

At 240, the continuous time-based test signal acquired at 230 can be transformed to a frequency domain test signal. The transformation may be performed in the same manner as with the reference signal at 230. For example, the continuous time-based test signal acquired at 230 may be digitized using A/D converter 116 or the processing unit 108. The digitized or discrete time-based test signal can be transformed to the frequency domain, using various transformations such as the fast Fourier transform. The transformation can similarly be repeated for test signals acquired for each additional test location. In some cases, as with the reference signal, the continuous time-based test signal may not be digitized prior to being transformed to the frequency domain.

At 250, the frequency domain test signal for the test location can be normalized. The frequency domain test signal can be normalized using the frequency domain reference signal generated at 220.

The frequency domain test signal may be normalized by, for each frequency of the frequency domain test signal, performing a complex division of a test signal component of the frequency domain test signal at that frequency by a reference signal component of the frequency domain reference signal at that frequency. In the example described above with reference to FIG. 5B, this may entail normalizing the test signal components for each of 2048 frequencies using the corresponding reference signal components for those same frequencies.

Figure 7:
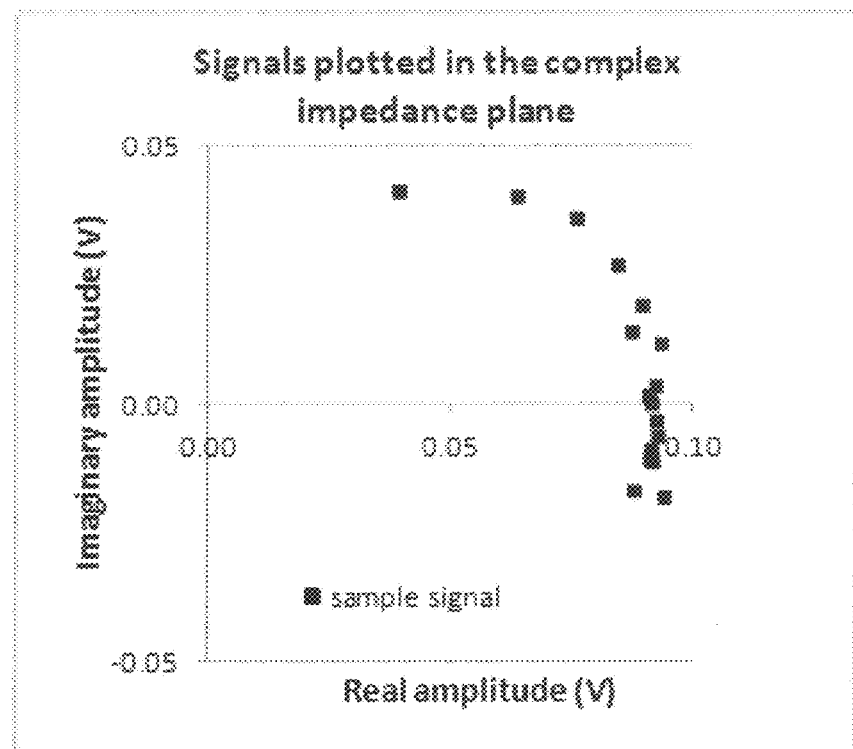
FIG. 7 is a plot of test signal components for a plurality of frequencies in a complex impedance plane.

Referring now to FIG. 7, shown therein is a plot of normalized test signal components for a plurality of frequencies in a complex impedance plane. These test signal components are examples of discrete frequency domain test signal components that may be generated at 240. The normalized test signal components shown in FIG. 7 correspond to test signal components for discrete frequencies from 244 to 2199 Hz plotted in a complex impedance plane representation. As FIG. 7 illustrates, the frequency domain test signal components (real and complex) can vary significantly across a range of frequencies. Typically, the frequency domain test signal components (real and complex) will be unique for each frequency and set of parameters.

At 260, a desired number of parameters, for example at least one parameter of interest of the structure can be identified for the test location. In some cases, the at least one parameter of interest for the test location may include at least two parameters. The parameters of interest may be parameters that are unknown at the test location. In some cases, the parameters of interest may be identified by a user interacting with the processing unit 108. For instance, the parameters of interest may be determined based on the purpose for the structural evaluation, based on previous evaluations of the structure, or evaluations of other test locations on the same or similar structures. Various parameters may be identified as parameters of interest. For example, the at least one parameter may include at least one of a structure thickness, a feature surface extent, a feature shape, a feature depth, a deposit thickness, a lift-off variation, a permeability variation, a conductivity variation, and a conductor gap, amongst others.

At 270, a parameter value for each of the at least one parameters of interest identified at 260 can be evaluated. Optionally, the parameters values for each of the parameters of interest can be evaluated simultaneously. For instance, where two or more parameters of interest are identified at 260, the parameters values for each of the two or more parameters of interest can be simultaneously, or substantially simultaneously, evaluated. The parameters of interest may be evaluated using various methods, such as the iterative method 300 shown in FIG. 3. Iterative method 300 may use analytical approximations or estimations for the frequency response of all parameters of interest over the frequency ranges analyzed and compare those estimations to the actual (normalized) test signal acquired.

Figure 3:
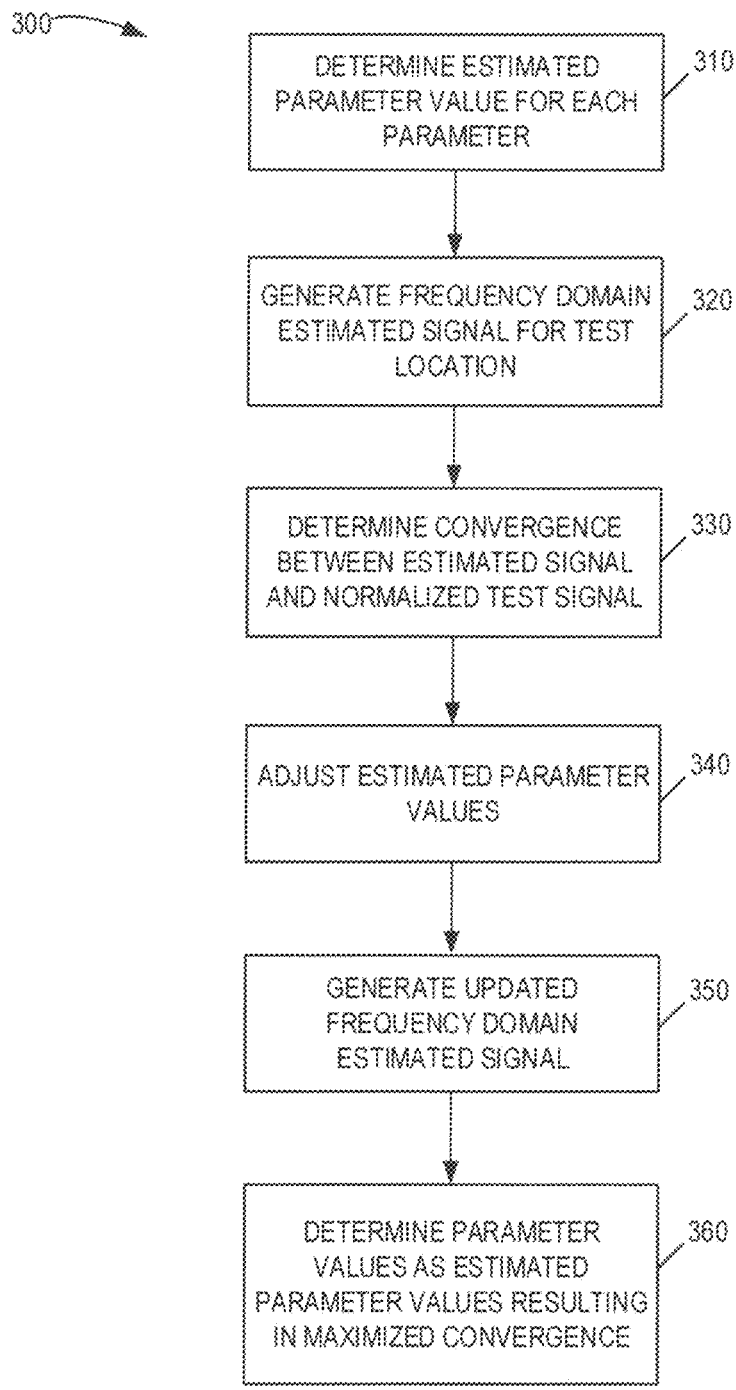
FIG. 3 is a flowchart of one example of a method for evaluating parameter values that may be used with the method of FIG. 2.

Referring now to FIG. 3, shown therein is a flowchart of one example of a method for evaluating parameter values that may be used with a method for non-destructive analysis of a structure such as method 200.

At 310, an estimated parameter value can be determined for each of the at least one parameters for the test location. Estimated parameters values may be determined in various ways. For example, the initial estimated parameters values may be determined randomly. Estimated parameter values may also be determined using expected parameter values from information known about the structure (e.g. material properties, reference thickness values, age etc.) that can be used to estimate changes in the structural parameters. In some cases, estimated parameter values may be determined from previous evaluations of the parameters at the test location or other test locations on the same or similar structures.

At 320, a frequency domain estimated signal can be generated for the test location using the estimated parameters values. The frequency domain estimated signal may be generated by applying analytical approximations to the frequency response (in both phase and amplitude) of all the parameters of interest. The approximated frequency response may be determined empirically, or using other estimation techniques such as integrating the skin depth expression for the structure over depth.

For example, the frequency domain estimated signal can be generated by determining a skin depth of the structure at each frequency in the normalized test signal. The frequency domain estimated signal can then be generated by modelling a test signal at the test point using the calculated skin depth for each frequency of the normalized test signal and the estimated parameter values.

The frequency dependence of a test signal response from applied interrogation waveforms (e.g. pulsed eddy current excitation) can often be estimated/approximated using expressions containing the skin depth, $\delta$.

The skin depth, $\delta$, can be calculated at each frequency for which a frequency domain test signal has been determined. This $\delta$ can then be used to calculate a provisional signal from the pre-determined constants and initial estimated parameter values representing the characteristics of the structure at the test location.

The skin depth $\delta$ may be defined as $$\delta = 50\sqrt{\text{resistivity}/(\text{frequency} * \text{relative permeability})}$$

where the skin depth in mm is obtained from resistivity in $\rho\Omega$-cm, frequency in inverse seconds and relative permeability (dimensionless).

The response signal amplitude of an infinitesimal void at depth x may be determined to be proportional to $e^{-2x/\delta}$. Similarly, the phase, $\varphi$, attributable to the response signal may be determined as $\varphi=2x/\delta$. Weighted integration of these quantities, over the range of the feature's depth, may be used to obtain an analytical expression for the frequency dependence of the estimated test response signal. Alternatively, an empirical expression or more elaborate calculations known to those skilled in the art may be used.

In some cases, changes in material properties may affect the skin depth $\delta$. For example, changes in material properties can affect the ratio of resistivity to relative permeability, and hence affect the skin depth. Accordingly, some embodiments may compensate for such material-properties changes (or potential changes). Compensation for material-property changes may be repeated at multiple test locations.

Optionally, a pair of response signal amplitudes can be measured at a test location. The pair of response signal amplitudes can be measured for two values of lift-off that differ by a known amount. The signal amplitudes may be acquired using a signal probe with its lift-off position (with respect to the test location) adjusted or by two separate probes having a known vertical offset. The skin depth variation (relative to a known reference location) may be determined from the pair of response signal amplitudes and the known difference in lift-off amount. Optionally, the process of determining the skin depth variation may be performed each test location.

The pair of response signal amplitudes can include a first response signal amplitude $A_{lo1}$ and a second response signal amplitude $A_{lo2}$. The first response signal amplitude can be the product of an empirically obtained frequency-dependent amplitude factor and the amplitude measured in response to a first interrogation signal applied from a first lift-off distance $d_{lo1}$ and the second response signal amplitude can be the product of the same frequency-dependent amplitude factor and the amplitude measured in response to a second interrogation signal applied from a second lift-off distance $d_{lo2}$. The first lift-off distance and second lift-off distance can have a defined lift-off pair difference (e.g. $\Delta d_{lo}=d_{lo1}-d_{lo2}$). The skin depth variation may then be determined using the first response signal amplitude, the second response signal amplitude and the lift-off pair difference.

An adjusted first response signal amplitude can be determined by subtracting 1 from the first response signal amplitude. Similarly, an adjusted second response signal amplitude can be determined by subtracting 1 from the second response signal amplitude. A property compensation ratio can be defined as a ratio of the adjusted first response signal amplitude and the adjusted second response signal amplitude.

An adjusted lift-off pair difference may also be determined by multiplying the lift-off pair difference by two. A logarithm of the property compensation ratio divided by the adjusted lift-off pair difference can be used to determine changes to the skin depth relative to the skin depth at some reference point. For instance, the inverse of the skin depth may be defined as the logarithm of the property compensation ratio divided by the adjusted lift-off pair difference:

$$\frac{1}{\delta} \propto \frac{\log\left(\frac{A_{lo1}-1}{A_{lo2}-1}\right)}{\Delta d_{lo}}$$

At 330, a convergence between the estimated signal and the normalized test signal can be determined. The convergence between the estimated signal and the normalized test signal may be determined as a similarity or difference measure between the two signals (e.g. an error value).

The convergence between the estimated signal and the normalized test signal can be determined by, for example, at each frequency of the normalized test signal, determining a residual signal value based on the difference between the estimated signal and the normalized test signal. The convergence between the estimated signal and the normalized test signal may be determined as a sum of the residual signal values for each frequency (a residual sum). In some cases, the residual signals values for each frequency can be weighted. For example, a reduction factor can be applied to residual values of frequencies with known sources of noise, to improve the convergence between the estimated signal and the normalized test signal by reducing or removing the contribution from specific-frequency noise. The frequency domain signal components for both the normalized test signal and the estimated signal may include both real and complex amplitudes at each frequency. Accordingly, the residual signal values may be determined by measuring a difference between the real components and a difference between the complex components for each frequency. In some cases, the residual signal value can be determined by squaring the residuals for each frequency and the convergence between the estimated signal and the normalized test signal may be determined as a sum of the squared residual values over all frequencies.

At 340, the estimated parameter values can be adjusted and an updated frequency domain estimated signal can be generated at 350. In general, steps 330-350 may be iteratively repeated until a desired convergence criterion is satisfied. That is, the estimated parameter values may be iteratively adjusted and a corresponding updated frequency domain estimated signal can be generated for each set of estimated parameters values.

This iterative process may continue until the convergence between the estimated signal and the normalized test signal is maximized (i.e. the error is minimized) or a desired convergence criterion is reached. For example, in some cases, the operating parameters may include a maximum evaluation time period or other constraints that prevent the process from continuing to iterate until all possible parameter values are evaluated. In other cases, the iterative process may stop once a desired maximum convergence (minimum error) between the estimated signal and the normalized test signal is reached, indicating sufficient agreement between the estimated signal and the normalized test signal. For example, where the convergence between the estimated signal and the normalized test signal is above a convergence threshold, no further iteration may be needed. The convergence threshold may be an operating parameter established by a user depending on the structure being examined and/or the purpose of the evaluation.

At 360, the parameter value for each of the parameters of interest can be determined as the estimated parameter value for that parameter used to generate the estimated signal that results in the maximized convergence between the estimated signal and the normalized test signal. That is, the set of parameter values used to generate the estimated response signal having the greatest agreement with the normalized test signal may be identified as the parameter values of the parameters of interest.

The determined parameter values may then be used to analyze the structure. In some cases, the frequency domain final estimated signal using the determined parameter values for the at least two parameters may be concurrently displayed along with the normalized frequency domain test signal using display 112. This may indicate to a user the level of convergence between the estimated signal and the normalized test signal, and indirectly provide an indication of the confidence level for the determined parameter values. Additionally or alternatively a value indicating the level of convergence between the signals may be displayed to the user.

In some cases, embodiments of the methods described herein, such as methods 200 and 300 (and method 400 described below), may be repeated for a plurality of additional test locations. The parameter values determined for each test location may then be used to model the structure being evaluated. The modelled structure may then be displayed to a user using display 112 to allow a visual inspection of the structure. This may enable a visual inspection of subsurface regions of the structure without damaging or destroying the structure.

In general, the determined parameter values and/or modelled structures can be stored using a database, such as may be provided by the memory unit of system 100. This may allow for future analysis, such as comparative analysis with structural evaluations performed at a different time or for similar structures.

Figure 4:
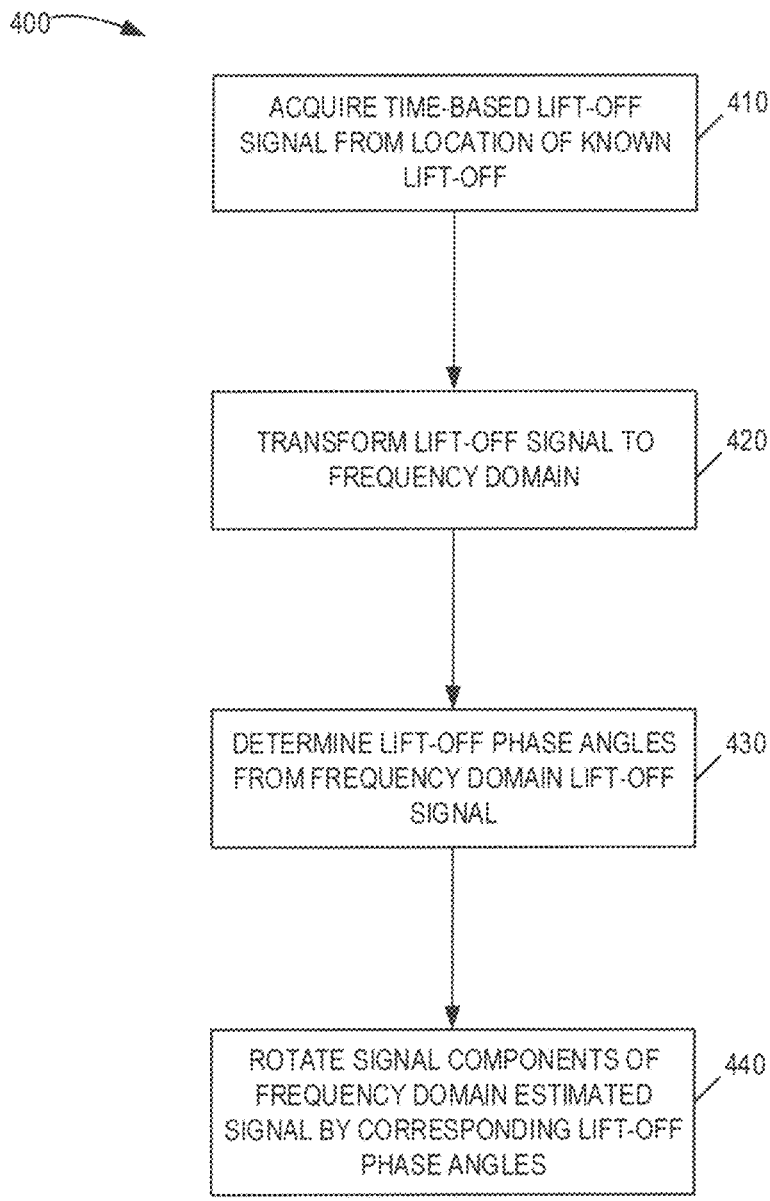
FIG. 4 is a flowchart of one example of a method for lift-off calibration that may be used with the method of FIG. 2.

Referring now to FIG. 4, shown therein is a flowchart of one example of a method for lift-off calibration that may be used with a method for non-destructive analysis of a structure such as method 200 and method 300. For instance, in some cases steps 410-430 of method 400 may be performed at any time prior to evaluation of the structure in step 270 of method 200. As well, in some cases, step 440 of method 400 may be performed each time a frequency domain estimated signal is generated (i.e. at 320 and 350).

Traditional eddy current analysis uses the convention that increasing lift-off gives a response signal aligned with the negative real axis. To correspond to conventional signal response analysis, the estimated signal components can be rotated at each frequency to have the conventional orientation (alternatively, the normalized test signal components could be rotated). The rotation angle can be determined from the angles obtained from a complex division of a lift-off signal by the reference signal.

At 410, a transient time based continuous lift-off signal can be acquired from a location of known lift-off from the structure using the interrogation unit 102. The location of known lift-off refers to a location having a known distance between the interrogation unit 102 and the surface of the structure or a calibration structure. For example, this may be obtained by positioning the interrogation unit over a non-conducting pad of known thickness on the surface of the structure. The signal may be acquired in a similar manner as with the acquired reference and test signals.

At 420, the transient time based continuous lift-off signal can be transformed to a frequency domain lift-off signal in a similar manner as with the test and reference signals. Using the same process and operating parameters to acquire transform each of the reference, test, and lift-off signals may ensure that the signals all have frequency domain signal components at the same frequencies. The frequency domain lift-off signal may include both real and complex signal components. The real and complex signal components can be used to identify a phase angle of the acquired lift-off signal at each frequency.

At 430, a plurality of lift-off phase angles can be determined from the frequency domain lift-off signals. The plurality of lift-off phase angles can include a lift-off phase angle for each frequency of the frequency domain lift-off signal. The lift-off phase angles can be used to calibrate the parameter evaluation process to account for variations in the frequency response at a test location due to unknown quantities of lift-off.

In some cases, the lift-off phase angle for a particular frequency may be determined by first normalizing the frequency domain lift-off signal with respect to the frequency domain reference signal. The real and complex signal components of the normalized lift-off signal at various frequencies can then be used to determine lift-off phase angles for those frequencies.

The frequency domain lift-off signal can be normalized by performing a complex division of the frequency domain lift-off signal components at each frequency by the frequency domain reference signal component at the corresponding frequency. For example, the complex division can be performed by the EXCEL worksheet function, IMDIV with arguments (lift-off, reference). The phase angle for each frequency can then be determined from the real and complex signal components resulting from the complex division at that frequency.

Figure 8:
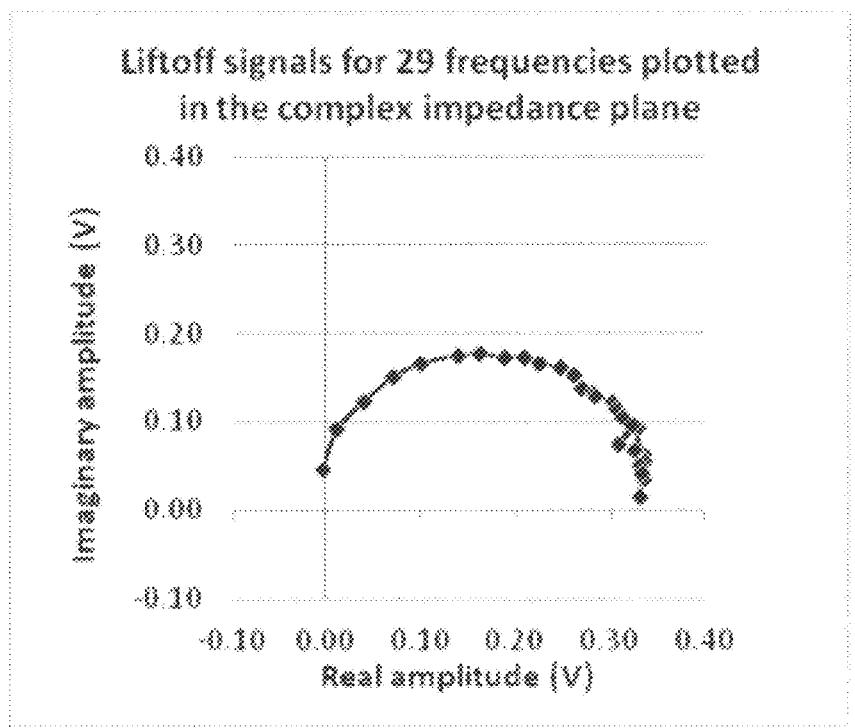
FIG. 8 is a plot of lift-off signal components for a plurality of frequencies in a complex impedance plane.

FIG. 8 shows an example plot of frequency domain lift-off signal components for a plurality of frequencies in a complex impedance plane. The plot shown in FIG. 8 corresponds to a lift-off signal acquired with a 1 mm lift-off. The rotational offset in the complex plane at each frequency can be deduced by performing trigonometry on the real and imaginary components of the result of the complex division. As shown in FIG. 8, the phase angle offset increases (in the clockwise direction) with increasing frequency, ranging from approximately 90 to 180 degrees over 29 different frequencies.

At 440, the signal components of the frequency domain estimated signal can be rotated at each frequency by the lift-off phase angle determined for that frequency. This may be done prior to determining the convergence between the estimated signal and the normalized test signal.

The lift-off phase calibration described above provides a phase angle offset that can be used to analyze other parameters of interest, such as material thickness. In some cases, a quantitative lift-off distance calibration, from data taken at different values of lift-off, may be performed if the probe-to-test-piece distance is to be extracted from the subsequent analysis. To determine a quantitative value of the actual lift-off distance, the calibration can be performed for a plurality of known lift-off values to determine a modelled lift-off relationship between the lift-off signal amplitude and probe-to-test-piece distance at each transformed frequency. In a manner analogous to that for other parameters in this analysis methods described herein, an unknown lift-off parameter value can then be determined through a convergence technique such as the minimization of residuals relative to a frequency-dependent expression (e.g. such as the modelled lift-off relationship). In this way, lift-off parameter values can be determined independently of other parameters.

An example is now provided where the parameters of interest include the remaining conductor thickness, lift-off, and feature extent (surface area). In other cases, other parameters may also be evaluated from the response signal. For the present simplified example, we will assume lift-off does not change during the measurement. The expression $$A = s(\delta/2)^{(1+p)}(e^{-2x/\delta} - e^{-2w/\delta})$$

can be used to estimate response signal amplitude and the expression $$\varphi = \varphi_0 + \varphi_1 + 1 + 2/\delta(we^{-2w/\delta} - xe^{-2x/\delta})/(e^{-2w/\delta} - e^{-2x/\delta})$$

can be used to estimate the phase of the response signal.

In the above expressions, w is the nominal wall thickness at the reference point, x is the remaining wall at the test point, s is the surface extent of the feature, p is an amplitude power parameter, $\varphi_0$ is a fixed frequency-independent phase offset parameter and $\varphi_l$ is the measured frequency-dependent lift-off offset. The surface extent, s, of the feature may be a fixed scale factor in cases where the feature is larger than the field sensing area of the probe, a fitted variable in cases where the feature is smaller than the sensing area, and a function with additional variables where the extent of the feature varies with depth. In the present example, x and s are the fitted variables we wish to extract.

Constants like w (the thickness at the reference point) and those that determine δ (frequency, material resistivity and material magnetic permeability) may be known from independent measurements or tabulated material properties. $\varphi_l$ can be determined obtained using lift-off calibration data by the process described above. Constants like $\varphi_0$ and p can be determined once for a series of measurements by forcing agreement between the analytical expressions and measurements taken at locations with known parameters Additional quantities, useful in other measurements, may include parameterizations of deposit thickness, permeability changes, and flaw shape, among others. The estimated signal components can also be rotated by the phase angle of the normalized lift-off signal at each frequency, as explained above at 440.

Figure 9:
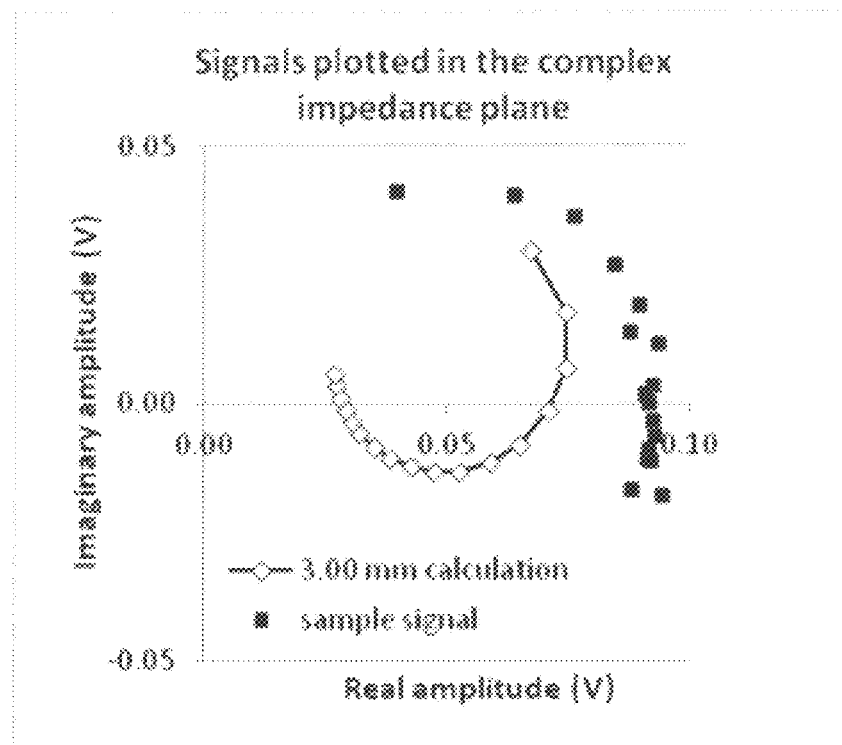
FIG. 9 is a plot of the test signal components of FIG. 7 and estimated signal components for the plurality of frequencies for an initial estimated signal.

FIG. 9 shows resulting estimated signal components with both real and complex amplitudes for one set of possible initial estimated parameter values, plotted on the same axes as the test response signal components of FIG. 7. FIG. 9 shows a plot for signal components of frequencies ranging from 244 Hz to 2199 Hz.

The residual signal values determined by comparing the estimated signal to the normalized test signal can be used to determine the convergence between the normalized test signal and the estimated test signal. For example, the difference between signal components at each frequency can be squared, and then summed for all frequencies (the convergence may be determined as the inverse of this value). The variable parameters (in the example above x, s, $\varphi_0$, and two amplitude offset parameters to centre the calculation on the data) can be adjusted to minimize the sum of residuals. The present example may use a multivariate least squares regression minimization process, but other optimization/minimization processes may be used.

As FIG. 9 illustrates, there may not be much similarity between the estimated signal and the normalized test signal (i.e. a low value of convergence). Accordingly, the initial estimated parameters may be adjusted iteratively and new estimated signals generated until the convergence between the estimated signal and the normalized test signal reaches a desired convergence criterion. In some cases, each time a new estimated signal is generated, the signal components can be rotated as explained above.

Figure 10:
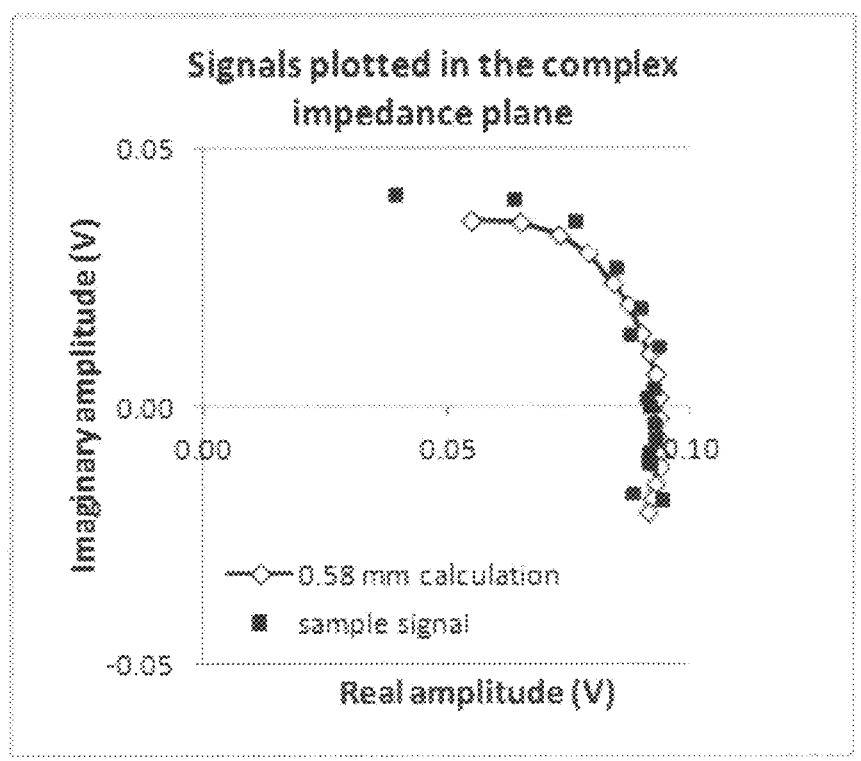
FIG. 10 is a plot of the test signal components of FIG. 7 and estimated signal components for the plurality of frequencies for a final estimated signal.

Referring now to FIG. 10, shown therein is a plot of the test signal components of FIG. 7 and estimated signal components for the plurality of frequencies for a final estimated signal. When the desired convergence is reached, the final estimated parameters values can be determined as the parameter values of the parameters of interest. In some cases, the final parameters may be displayed concurrently with the normalized test signal components, as shown in FIG. 10.

Figure 6:
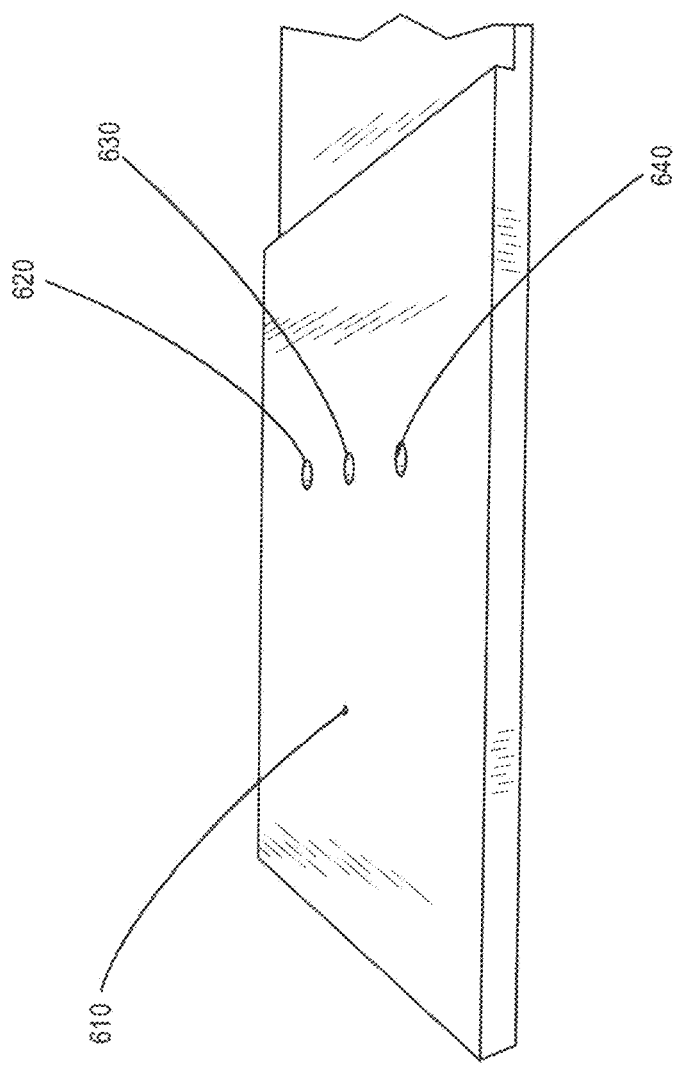
FIG. 6 is an image of an aluminum test structure analyzed using an example method for non-destructive analysis of a structure as described herein.

Referring now to FIG. 6, shown therein is an image of an aluminum alloy structure analyzed using an example method for non-destructive analysis of a structure as described herein. The frequency domain signal components shown in FIGS. 7-10 described above correspond to signal components generated from evaluation of the alloy structure shown in FIG. 6.

The aluminum alloy 5052 structure shown in FIG. 6 has a number of visible machined features 610, 620, 630 and 640. The aluminum alloy structure was evaluated for wall thickness. While the aluminum alloy structure shown in FIG. 6 is non-ferromagnetic (relative permeability=1), ferromagnetic materials (relative permeability >1) may also be tested using embodiments described herein. Similar trials have also been performed on a variety of aluminum samples for detection limits, thickness response, lift-off response, and response to the surface extent of the indications. Other possible applications may include other conductive materials, including ferromagnetic and non-ferromagnetic materials and other geometries (cracks, pits, general wall loss, gaps between conductive layers, probe-to-conductor distance, ferromagnetic features, etc.).

Thick aluminum, as used in this example, can pose problems for conventional eddy current testing. This may be because normally accessible frequencies tend to give shallow skin depths. Hence, there may be low sensitivity to features on the far side of the material. As a result, pulsed eddy current techniques are often chosen over conventional eddy current testing for such materials. The test piece shown in FIG. 6 is nominally 8 mm thick and has 1.7-mm and 4-mm diameter flat-bottom holes of various depths, including through-wall penetration. The sample has additional regions of different base thickness, which are not used in the present test. The segment shown is measured; it has a 1.7-mm through-hole 610 and 0 mm, 0.5 mm, and 1.0 mm remaining wall for the 4-mm diameter holes 620, 630 and 640 respectively.

Embodiments described herein can be applied to the analysis of individual locations on structures, as well as the analysis of multiple locations, such as a strip or two dimensional area. Automated techniques for scanning a strip or two dimensional areas can be used to permit geometrical reconstruction of the structure being evaluated and the parameters of interest. "Automation" here may refer to the movement of the probe, to the acquisition and transformation of the data, to the minimization of residuals to produce a full set of structural parameters, or even to the display of a geometrical image of the structure.

Figure 11:
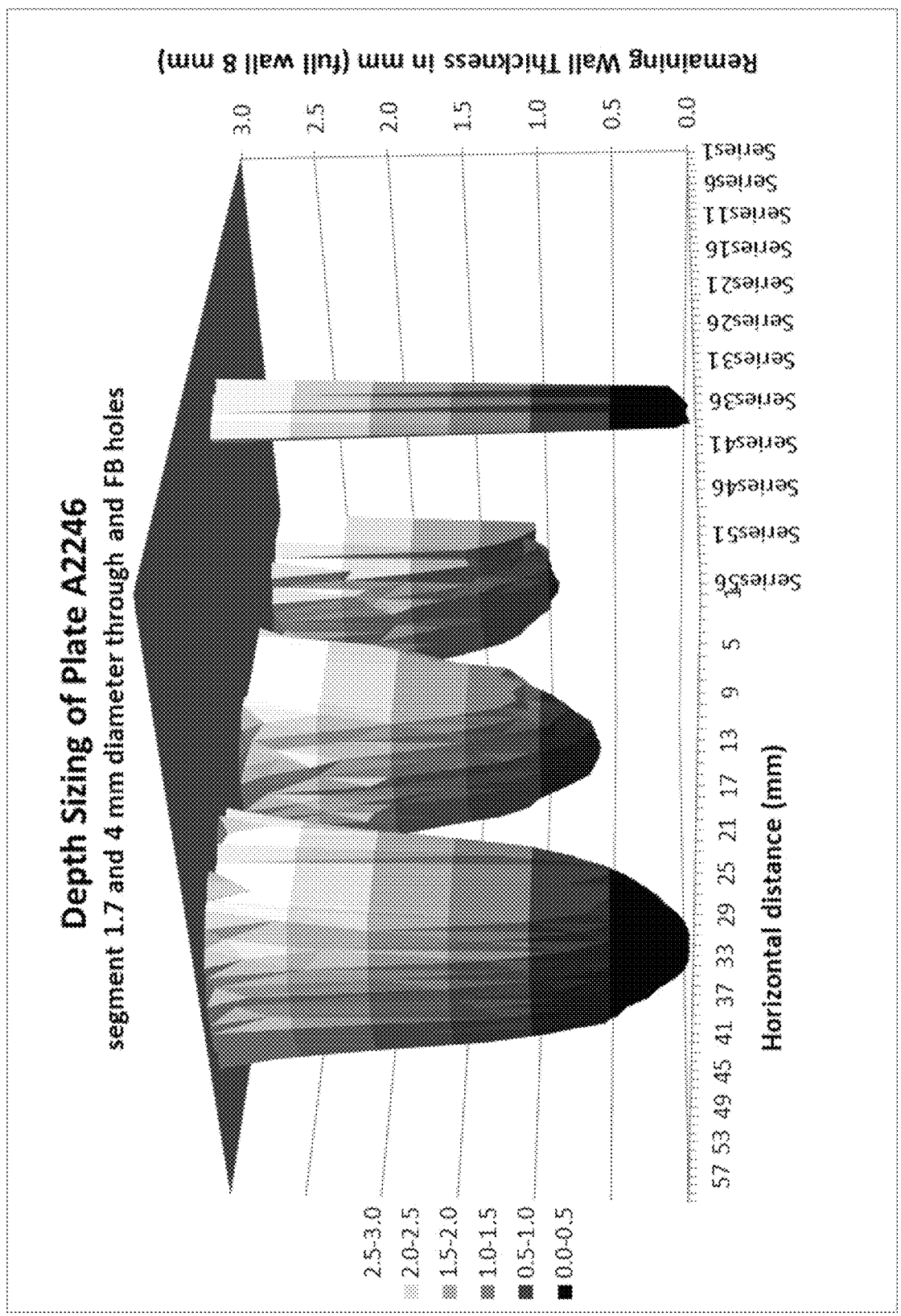
FIG. 11 is a plot of an example modelled structure for depth parameter values generated based on analysis of test locations from a two-dimensional scan of the aluminum alloy structure of FIG. 6.

Referring now to FIG. 11, shown therein is a plot of an example modelled structure generated based on analysis of test locations from a two-dimensional scan of the aluminum alloy structure of FIG. 6. FIG. 11 illustrates a three-dimensional plot of parameters values determined for remaining wall thickness of the aluminum alloy structure shown in FIG. 6. As FIG. 11 illustrates, the 1.7 and 4.0 mm through holes are correctly identified as modelled through holes 1110 and 1120 respectively and the 4 mm holes with 0.5 and 1.0 mm remaining wall (1130 and 1140 respectively) are also observed with quantitatively correct depths. Because the sensing area of the probe used (a side-by-side transmit-receive pair of 20-mm diameter coils, with 20 mm centre-to-centre separation) was larger than the features measured, the holes appear to extend over much greater surface area than they actually cover.

Figure 12:
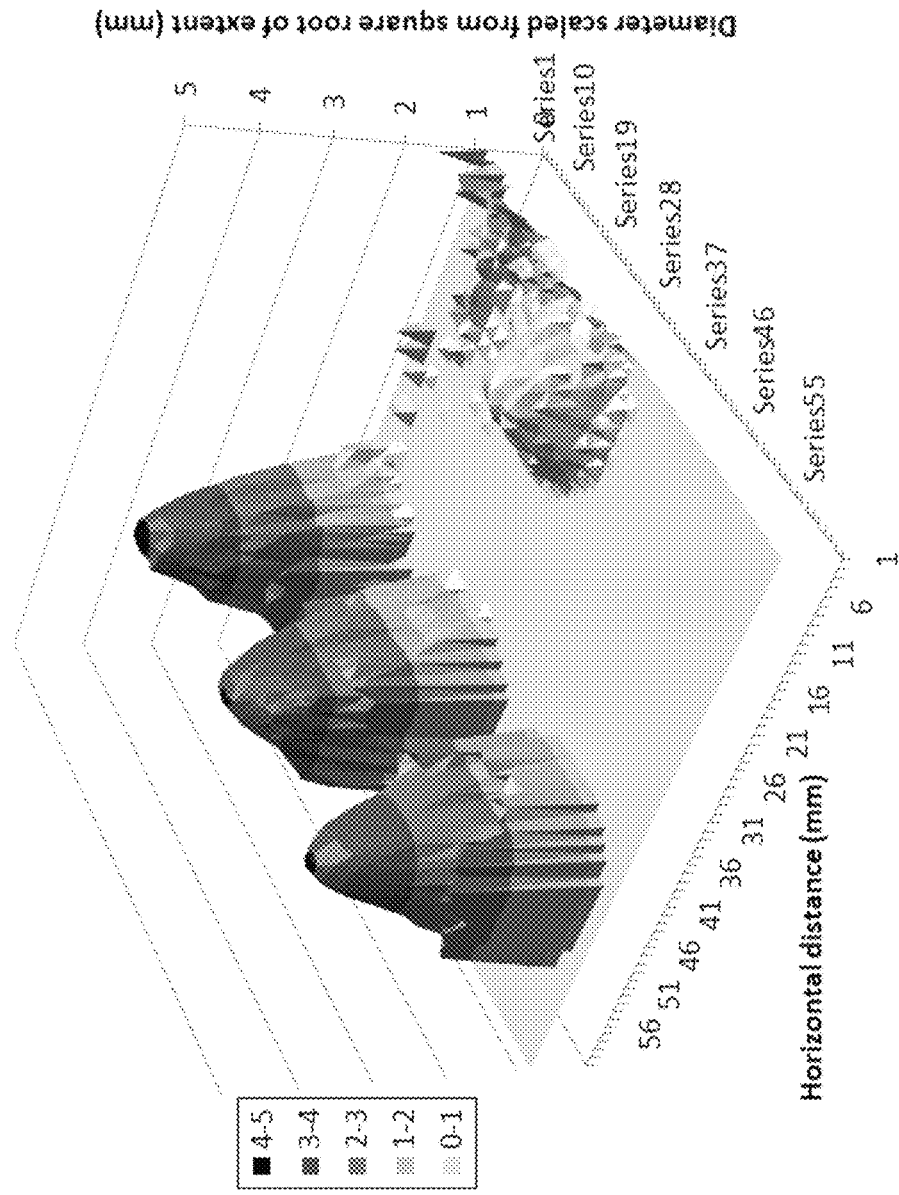
FIG. 12 is a plot of another example modelled structure for extent parameter values generated based on the example modelled structure of FIG. 11.

Referring now to FIG. 12, shown therein is a plot of an areal extent parameter value (in mm diameter) determined for the structure of FIG. 6 using an embodiment of the methods described herein. In FIG. 12, spurious sub-millimetre values arising from signal noise are suppressed by setting all sub-millimetre values to 1.0 mm.

The surface extent, s, obtained in the measurements, may be helpful in correcting the graphical representation. The extent parameter, here calibrated by taking a square root and scaling, is shown in FIG. 12. The plot indicates that the large holes (indicated by 1220, 1230 and 1240) reach a maximum of 4.0 to 4.1 mm diameter and that the smaller-diameter hole (indicated by 1210) reaches a maximum diameter of 1.9 mm. These values correspond closely to the nominal machined dimensions.

Figure 13:
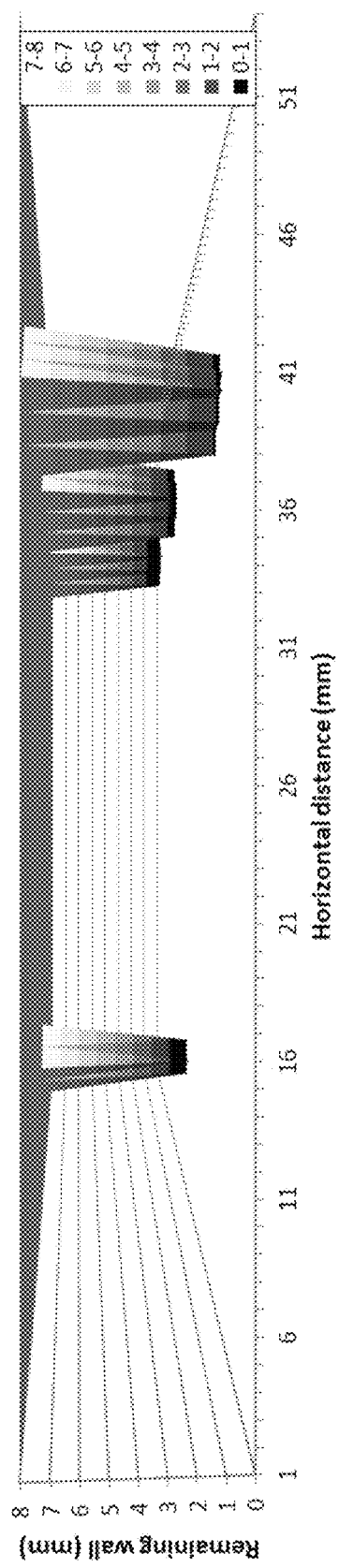
FIG. 13 is a plot of a further example modelled structure for multiple parameter values generated based on the example modelled structure of FIG. 11.

Referring now to FIG. 13, shown therein is a plot of a further example modelled structure generated based on the example modelled structure of FIG. 11. FIG. 13 shows a reconstructed model of various parameters of interest of the alloy of FIG. 6. The model shown in FIG. 13 was generated by further processing the parameter data. The centre of each hole location was determined by finding the location of the local maximum of the extent parameter in FIG. 12, and the diameter of each hole was taken from the value at each local maximum. This information was combined with the depth values from FIG. 11 to produce the composite plot in FIG. 13. As can be seen in comparison to FIG. 6, the model shown in FIG. 13 corresponds well to the alloy structure being evaluated with modelled features 1310, 1320, 1330 and 1340 corresponding to structural features 610, 620, 630 and 640 respectively.

Figure 14:
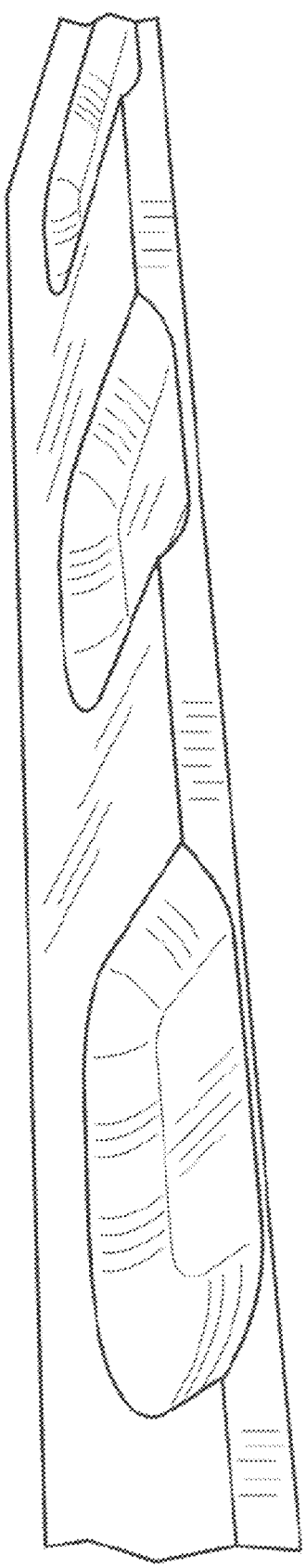
FIG. 14 is an image of another example aluminum test structure.

Referring now to FIG. 14, shown therein is an image of another example aluminum test structure. The aluminum test structure shown in FIG. 14 is scalloped with features that are large compared to the probe sensing area that was used. The test structure, nominally 8 mm thick, had scalloped regions with 1 mm, 2 mm, and 4 mm remaining wall thickness. The test structure of FIG. 14 was evaluated as described herein. Quantitative analysis was performed using the s parameter as a fixed calibrated value.

Figure 15:
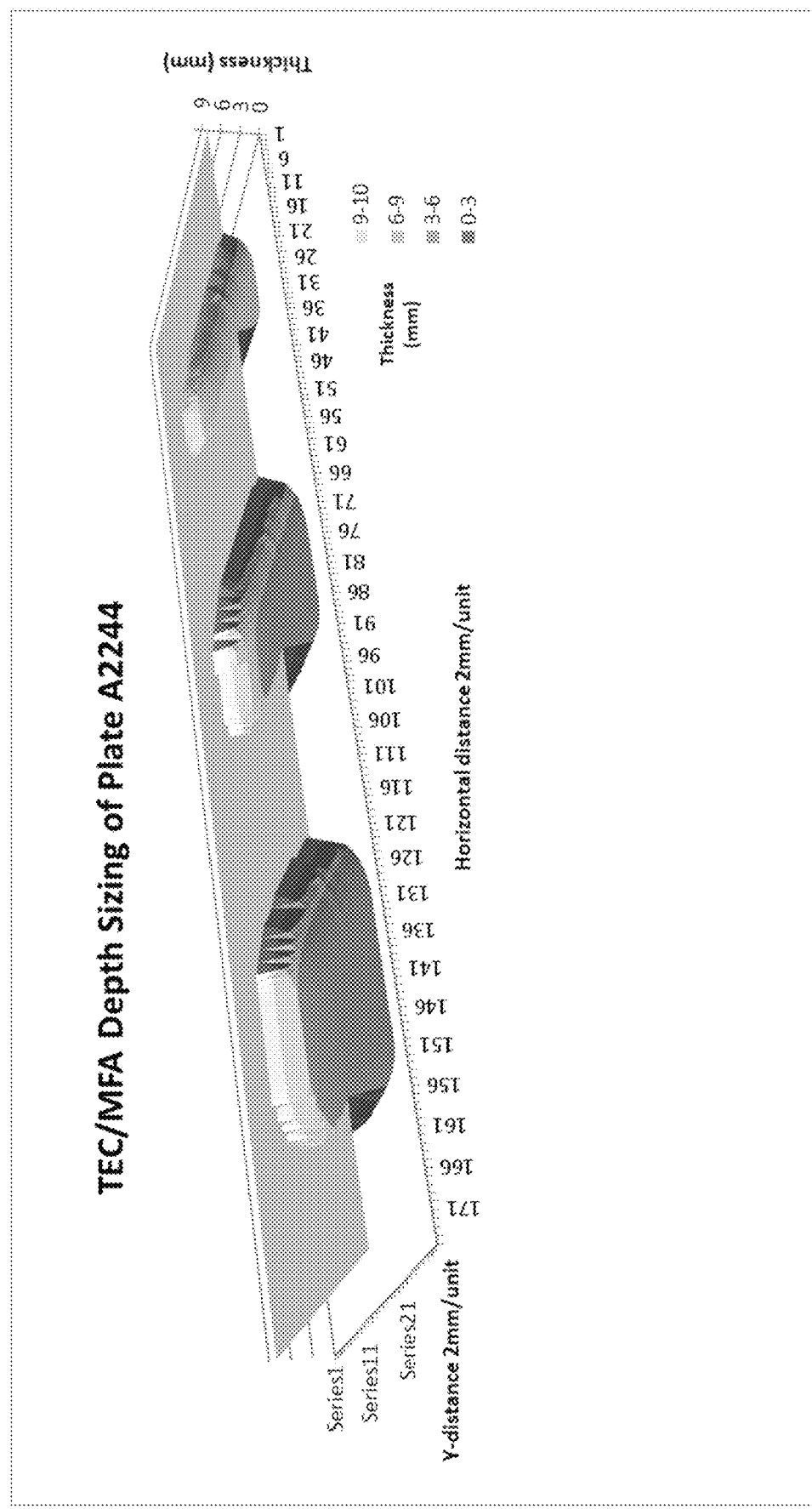
FIG. 15 is a plot of an example modelled structure generated based on analysis of test locations from a two-dimensional scan of the aluminum test structure of FIG. 14.

FIG. 15 shows a plot of an example modelled structure generated based on analysis of test locations from a two-dimensional scan of the aluminum test structure of FIG. 14.

As FIG. 15 illustrates, a realistic three-dimensional representation of the test structure was possible using embodiments described herein.

What has been described above has been intended to be illustrative of the invention and non-limiting and it will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

The invention claimed is:

1. A method for non-destructive analysis of a structure, the method comprising:
   a) applying an interrogation waveform to a reference location on one of the structure and a calibration structure using a signal transmitter coupled to a function generator;
   b) applying the interrogation waveform to a test location on the structure using the signal transmitter;
   c) acquiring a transient time based continuous reference signal from the reference location using a sensor;
   d) transforming the transient time based continuous reference signal to a frequency domain reference signal using a processor coupled to the sensor;
   e) acquiring a transient time based continuous test signal from the test location using the sensor;
   f) transforming the transient time based continuous test signal to a frequency domain test signal using the processor;
   g) identifying at least one parameter of interest of the structure at the test location using the processor; and
   h) evaluating a parameter value for each of the at least one parameter of interest by using the processor configured to:
      i) determine an estimated parameter value for each of the at least one parameters;
      ii) generate a frequency domain estimated signal for the test location using the estimated parameter values;
      iii) determine a convergence between the estimated signal and the test signal;
      iv) iteratively adjust the estimated parameter values and generating an updated frequency domain estimated signal; and
      v) for each of the at least one parameters, determine the parameter value as the estimated parameter value for that parameter used to generate the estimated signal that results in a maximized convergence between the estimated signal and the test signal.

2. The method of claim 1, further comprising:
   a) prior to evaluating the parameter value for each of the at least one parameter of interest, normalizing the frequency domain test signal by, for each frequency of the frequency domain test signal, performing a complex division of a test signal component of the frequency domain test signal at that frequency by a reference signal component of the frequency domain reference signal at that frequency.

3. The method of claim 1, further comprising:
   a) acquiring a transient time based continuous lift-off signal from a location of known lift-off from the one of the structure and the calibration structure;
   b) transforming the transient time based continuous lift-off signal to a frequency domain lift-off signal;
   c) determining a plurality of lift-off phase angles from the frequency domain lift-off signal, one lift-off phase angle for each frequency of the frequency domain lift-off signal; and
   d) prior to determining the convergence between the estimated signal and the test signal, for each frequency of the test signal, rotating a signal component of the estimated signal at that frequency by the lift-off phase angle determined for that frequency.

4. The method of claim 3, wherein the lift-off phase angle for a particular frequency is determined by:
   a) performing a complex division of a lift-off signal component of the frequency domain lift-off signal at the particular frequency by the reference signal component of the frequency domain reference signal for the particular frequency; and
   b) determining the lift-off phase angle for the particular frequency from the real and complex signal components resulting from the complex division.

5. The method of claim 1, wherein the at least one parameter of interest comprises a lift-off distance and the method further comprises:
   a) acquiring a plurality of transient time based continuous lift-off calibration signals from a corresponding plurality of lift-off calibration locations, each lift-off calibration location having a different lift-off value from the one of the structure and the calibration structure;
   b) transforming each of the transient time based continuous lift-off calibration signals to a frequency domain lift-off calibration signal;
   c) generating an estimated lift-off model using the lift-off values for each of the lift-off calibration locations and corresponding frequency domain lift-off calibration signal; and
   d) generating the frequency domain estimated signal for the test location by applying the estimated lift-off model to the estimated parameter value for the lift-off distance.

6. The method of claim 1, wherein the at least one parameter of interest comprises at least two parameters, and the parameter values for each of the at least two parameters are evaluated simultaneously.

7. The method of claim 1, wherein the frequency domain estimated signal is generated by:
   a) determining a skin depth of the structure at each frequency of the test signal; and
   b) generating the frequency domain estimated signal by modelling a test signal estimate at the test point using the calculated skin depth for each frequency of the test signal and the estimated parameter values.

8. The method of claim 1, further comprising:
   a) generating a frequency domain final estimated signal using the determined parameter values for the at least one parameter; and
   b) concurrently displaying the frequency domain final estimated signal and the frequency domain test signal.

9. The method of claim 1, further comprising:
   a) acquiring at least one additional transient time based continuous test signal, each additional transient time based continuous test signal being acquired from an additional test location on the structure;
   b) transforming each of the additional transient time based continuous test signals to a frequency domain additional test signal; and c) for each frequency domain additional test signal, evaluating an additional parameter value of the at least one parameter of the structure at the corresponding additional test location by
  i) determining an additional estimated parameter value for each of the at least one parameters;
  ii) generating an additional frequency domain estimated signal for that additional test location using the additional estimated parameter values;
  iii) determining an additional convergence between the additional estimated signal and the additional test signal;
  iv) iteratively adjusting the additional estimated parameter values and generating an updated additional frequency domain estimated signal; and
  v) for each of the at least one parameters, determining the additional parameter value as the additional estimated parameter value for that parameter used to generate the additional estimated signal that results in a maximized convergence between the additional estimated signal and the additional test signal.

10. The method of claim 9 further comprising:
a) modelling the structure using the parameter values determined for each test location of the structure; and
b) displaying the modelled structure.

11. A system for non-destructive analysis of a structure, the system comprising:
a) a function generator for generating an interrogation waveform;
b) an interrogation unit coupled to the function generator, the interrogation unit including a signal transmitter and a sensor, wherein the signal transmitter is configured to
  i) apply the interrogation waveform to a reference location on one of the structure and a calibration structure; and
  ii) apply the interrogation waveform to a test location on the structure;
and the sensor is configured to
  i) acquire a transient time based continuous reference signal from the reference location; and
  ii) acquire a transient time based continuous test signal from the test location;
c) a processor coupled to the probe, the processor configured to
  i) transform the transient time based continuous reference signal received from the sensor to a frequency domain reference signal;
  ii) transform the transient time based continuous test signal received from the sensor to a frequency domain test signal;
  iii) identify at least one parameter of interest of the structure at the test location; and
  iv) evaluate a parameter value for each of the at least one parameters of interest by
    a. determining an estimated parameter value for each of the at least one parameters;
    b. generating a frequency domain estimated signal for the test location using the estimated parameter values;
    c. determining a convergence between the estimated signal and the normalized test signal;
    d. iteratively adjusting the estimated parameter values and generating an updated frequency domain estimated signal; and
    e. for each of the at least one parameters, determining the parameter value as the estimated parameter value for that parameter used to generate the estimated signal that results in a maximized convergence between the estimated signal and the normalized test signal; and
d) a display coupled to the processor for displaying the determined parameter values of the structure.

12. The system of claim 11, wherein the processor is further configured to:
a) prior to evaluating the parameter value for each of the at least one parameters of interest, normalize the frequency domain test signal by, for each frequency in the frequency domain test signal, performing a complex division of a test signal component of the frequency domain test signal at that frequency by a reference signal component of the frequency domain reference signal at that frequency.

13. The system of claim 11, wherein:
a) the transmitter is further configured to apply the interrogation waveform at a location of known lift-off from the one of the structure and the calibration structure;
b) the sensor is further configured to acquire a transient time based continuous lift-off signal from the location of known lift-off; and
c) the processor is further configured to
  i) transform the transient time based continuous lift-off signal received from the sensor to a frequency domain lift-off signal;
  ii) determine a plurality of lift-off phase angles from the frequency domain lift-off signal, one lift-off phase angle for each frequency of the frequency domain lift-off signal; and
  iii) prior to determining the convergence between the estimated signal and the test signal, for each frequency of the test signal, rotate a signal component of the estimated signal at that frequency by the lift-off phase angle determined for that frequency.

14. The system of claim 13, wherein the processor is configured to determine the lift-off phase angle for a particular frequency by:
a) performing a complex division of a lift-off signal component of the frequency domain lift-off signal at the particular frequency by the reference signal component of the frequency domain reference signal for the particular frequency; and
b) determining the lift-off phase angle for the particular frequency from the real and complex signal components resulting from the complex division.

15. The system of claim 11, wherein:
a) the at least one parameter of interest comprises a lift-off distance;
b) the transmitter is further configured to apply the interrogation waveform at a plurality of lift-off calibration locations, each lift-off calibration location having a different lift-off value from the one of the structure and the calibration structure;
c) the sensor is further configured to acquire a corresponding plurality of transient time based continuous lift-off calibration signals from the plurality of lift-off calibration locations; and
d) the processor is further configured to
  i) transform each of the transient time based continuous lift-off calibration signals to a frequency domain lift-off calibration signal;
  ii) generate an estimated lift-off model using the lift-off values for each of the lift-off calibration locations and corresponding frequency domain lift-off calibration signal; and iii) generate the frequency domain estimated signal for the test location by applying the estimated lift-off model to the estimated parameter value for the lift-off distance.

16. The system of claim 11, wherein the at least one parameter of interest comprises at least two parameters and the processor is configured to evaluate the parameter values for each of the at least two parameters simultaneously.

17. The system of claim 11, wherein the processor is configured to generate the frequency domain estimated signal by:
   a) determining a skin depth of the structure at each frequency of the test signal; and
   b) generating the frequency domain estimated signal by modelling a test signal estimate at the test point using the calculated skin depth for each frequency of the test signal and the estimated parameter values.

18. The system of claim 11, wherein the processor is further configured to:
   a) generate a frequency domain final estimated signal using the determined parameter values for each of the at least one parameters; and
   b) concurrently display the frequency domain final estimated signal and the frequency domain test signal using the display.

19. The system of claim 11, wherein:
   a) the transmitter is further configured to apply the interrogation waveform to at least one additional test location on the structure;
   b) the sensor is further configured to acquire at least one additional transient time based continuous test signal, each additional transient time based continuous test signal being acquired from a corresponding additional test location;
   c) the processor is further configured to
      i) transform each of the additional transient time based continuous test signals received from the sensor to a corresponding frequency domain additional test signal; and
      ii) for each frequency domain additional test signal, evaluate an additional parameter value of the at least one parameter of the structure at the corresponding additional test location by
      iii) determining an additional estimated parameter value for each of the at least one parameters;
      iv) generating an additional frequency domain estimated signal for that additional test location using the additional estimated parameter values;
      v) determining an additional convergence between the additional estimated signal and the additional test signal;
      vi) iteratively adjusting the additional estimated parameter values and generating an updated additional frequency domain estimated signal; and
      vii) for each of the at least one parameters, determining the additional parameter value as the additional estimated parameter value for that parameter used to generate the additional estimated signal that results in a maximized convergence between the additional estimated signal and the normalized additional test signal.

20. The system of claim 19 wherein the processor is further configured to:
   a) model the structure using the parameter values determined for each test location of the structure; and
   b) display the modelled structure using the display.

* * * * *